US 7,867,503 B2

(12) United States Patent
Gargano et al.

(10) Patent No.: US 7,867,503 B2
(45) Date of Patent: *Jan. 11, 2011

(54) **CHIMERIC RECOMBINANT ANTIGENS OF *TOXOPLASMA GONDII***

(75) Inventors: Nicola Gargano, Rome (IT); Elisa Beghetto, Rome (IT); Andrea Spadoni, Rome (IT)

(73) Assignee: Sigma-Tau Industrie Farmaceutiche Riunite S.p.A., Rome (IT)

( * ) Notice: Subject to any disclaimer, the term of this patent is extended or adjusted under 35 U.S.C. 154(b) by 0 days.

This patent is subject to a terminal disclaimer.

(21) Appl. No.: 11/899,754

(22) Filed: Sep. 6, 2007

(65) Prior Publication Data

US 2009/0092630 A1    Apr. 9, 2009

Related U.S. Application Data

(63) Continuation-in-part of application No. PCT/EP2006/001760, filed on Feb. 27, 2006.

(51) Int. Cl.
*A61K 39/012* (2006.01)
(52) U.S. Cl. .............. 424/273.1; 424/185.1; 424/184.1; 424/193.1; 424/265.1; 424/192.1; 530/350
(58) Field of Classification Search ........................ None
See application file for complete search history.

(56) References Cited

U.S. PATENT DOCUMENTS

| | | | |
|---|---|---|---|
| 4,877,726 A | 10/1989 | Suzuki | |
| 5,215,917 A | 6/1993 | De Araujo | 435/252.33 |
| 5,633,139 A | 5/1997 | Prince | |
| 5,665,542 A | 9/1997 | Prince | |
| 5,686,575 A | 11/1997 | Prince | |
| 5,962,654 A | 10/1999 | Duncombe | |
| 5,976,553 A | 11/1999 | Kim | |
| 6,221,619 B1 | 4/2001 | Maine | |
| 6,265,176 B1 | 7/2001 | Lin | |
| 6,392,014 B1 | 5/2002 | Cesbron | |

FOREIGN PATENT DOCUMENTS

| | | |
|---|---|---|
| CN | 1450087 | 10/2003 |
| EP | 0 082 745 | 6/1983 |
| EP | 0 301 961 | 2/1989 |
| EP | 0 391 319 | 10/1990 |
| EP | 0 431 541 | 6/1991 |
| EP | 0 724 016 | 7/1996 |
| EP | 0 751 147 | 1/1997 |
| EP | 0 710 724 | 5/1998 |
| FR | 2226468 | 11/1974 |
| FR | 2702491 | 9/1994 |
| IT | 1196817 | 11/1988 |
| JP | 54044016 | 4/1979 |
| JP | 11225783 | 8/1999 |
| JP | 2000300278 | 10/2000 |
| SU | 533376 | 10/1976 |
| WO | 89/05658 | 6/1989 |
| WO | 89/08700 | 9/1989 |
| WO | 89/12683 | 12/1989 |
| WO | 92/01067 | 1/1992 |
| WO | 92/02624 | 2/1992 |
| WO | 92/11366 | 7/1992 |
| WO | 94/17813 | 8/1994 |
| WO | 96/02654 | 2/1996 |
| WO | 97/27300 | 7/1997 |
| WO | 98/20734 | 5/1998 |
| WO | 99/32633 | 7/1999 |
| WO | 99/57295 | 11/1999 |
| WO | 99/61906 | 12/1999 |
| WO | 99/66043 | 12/1999 |
| WO | 01/63283 | 3/2001 |
| WO | 01/64243 | 9/2001 |
| WO | 03/080839 | 2/2003 |
| WO | 03/080839 A2 | 10/2003 |
| WO | 2004/031358 A2 | 4/2004 |

OTHER PUBLICATIONS

Greenspan et al (Nature Biotechnology 7: 936-937, 1999).*
Chothia et al (The Embo Journal, 1986, 5/4:823-26).*
Murphy et al. Pediatr. Infect. Dis. J. 1989. 8: S66-S68.*
Yamanaka et al (J. Pediatrics. 1993. 122(2): 212-218).*
Yang, Chung-Dar et al. "Protective immunity against *Toxoplasma gondii* in mice induced by chimeric protein rSAG1/2". Parasitology Research, vol. 92, No. 1, Jan. 2004, pp. 58-64.
Beghetto, Elisa et al. "A Combination of Antigenic Regions of *Toxoplasma gondii* Microneme Proteins Induces Protective Immunity against Oral Infection with Parasite Cysts". Journal of Infectious Diseases, 191, Feb. 2005, pp. 637-645.
Beghetto, Elisa et al. "Identification of a human immunodominant B-cell epitope within the GRA1 antigen of *Toxoplasma gondii* by phage display of cDNA libraries". International Journal of Parasitology, Pergamon Press, GB, vol. 31, No. 14, Dec. 2001, pp. 1659-1668.
Hiszczynska_Sawicka Elzbieta et al. "High yield expression and single-step purification of *Toxoplasma gondii* SAG1, GRA1, and GRA7 antigens in *Escherichia coli*". Protein Expression and Purification, vol. 27, No. 1, Jan. 2003, pp. 150-157.
PCT International Search Report for PCT/EP2006/001760 filed on Feb. 27, 2006 in the name of Kenton SRL.
PCT Written Opinion for PCT/EP2006/001760 filed on Feb. 27, 2006 in the name of Kenton SRL.
PCT International Preliminary Report on Patentability for PCT/EP2006/001760 filed on Feb. 27, 2006 in the name of Kenton SRL.
Beaman et al., "Principles and Practice of Infectious Diseases", 4th Ed., Churchill Livingstone Inc., New York, 1995, pp. 2455-2475.
Beghetto et al., "Molecular dissection of the human B-cell response against *Toxoplasma gondii* infection by lambda display of cDNA libraries", International Journal for Parasitology, 2003, 33:163-173.
Bermudes et al., "Cloning of a eDNA encoding the dense granule protein GRA3 from *Toxoplasma gondii*", Mol. Biochem. Parasitol., 1994, 68:247-257.

(Continued)

*Primary Examiner*—Jennifer E Graser
(74) *Attorney, Agent, or Firm*—Steinfl & Bruno LLP

(57) ABSTRACT

A method for treatment or prevention of *Toxoplasma gondii* infections pharmaceutical composition comprising an antigen fragments of *Toxoplasma gondii* in the form of a chimeric fusion product or a nucleotide sequence coding for the chimeric fusion product and a method of using the chimeric fusion product or nucleotide sequence coding therefor.

21 Claims, 6 Drawing Sheets

OTHER PUBLICATIONS

Bonhomme et al., "Quantitative Immunolocalization of a P29 Protein (GRA7), a New Antigen of *Toxoplasma gondii*", J. Histochem. Cytochem., 1998, 46:1411-1421.

Burg et al., "Molecular Analysis of the Gene Encoding the Major Surface Antigen of *Toxoplasma gondii*", J. Immunol., 1988, 141:3584-3591.

Cesbron-Delauw, et al., "Molecular characterization of a 23-kilodalton major antigen secreted by *Toxoplasma gondii*", 1989 P.N.A.S. USA 86, 7537-41.

Cohen, J.S., "Designing antisense oligonucleotides as pharmaceutical agents", Trends in Pharm. Sci., 10,435, 1989.

Cooney et al., "Site-Specific Oligonucleotide Binding Represses Transcription of the Human *c-myc* Gene in Vitro", Science 241, 456, 1988).

Dervan et al., "Second Structural Motif for Recognition of DNA by Oligonucleotide-Directed Triple-Helix Fonnation", Science 251, 1360, 1991.

Garcia-Réguet et al., "The microneme protein MIC3 of *Toxoplasma gondii* is a secretory adhesin that binds to both the surface of the host cells and the surface of the parasite", Cellular Microbiol., 2000, 2:353-364.

Harning et al., "Recombinant *Toxoplasma gondii* Surface Antigen 1 (P30) Expressed in *Escherichia coli* Is Recognized by Human Toxoplasma-Specific Immunoglobulin M (IgM) and IgG Antibodies", Clinical and Diagnostic Laboratory Immunology, May 1996, 355-357.

Hauser, William E. et al., "Augmentation of NK Activity by Soluble and Particulate Fractions of *Toxoplasma gondii*", The Journal of Immunology, vol. 131, No. 1, Jul. 1983, pp. 458-463.

Jacobs et al., "Identification and heterologous expression of a new dense granule protein (GRA7) from *Toxoplasma gondii*", Mol. Biochem. Parasitol. 91, 1998, 237-49.

Lecordier al., "Characterization of a dense granule antigen of *Toxoplasma gondii* (GRA6) associated to the network of the parasitophorolls vacuole", Mol. Biochem. Parasitol. 1995, 70, 85-94.

Lee et al., "Complexes formed by (Pyrimidine)n (purine)n DNAs on lowering the pH are three-stranded", Nucleic Acids Res 6,3073, 1979.

Luft, B.J., Remington J.S., "Toxoplasmic Encephalitis in AIDS", 1992, Clin. Infect. Dis. 15, 211-22.

McCabe and Remington, "Toxoplasmosis; The Time Has Come", N. Engl. J. Med. 1988, 318-313-5.

Meinkoth et al. "Hybridization of Nucleic Acids Immobilized on Solid Supports",Analytical Biochemistry 138,267-284, 1984.

Mevelec et al., "Molecular cloning of GRA4, a *Toxoplasma gondii* dense granule protein, recognized by mucosal IgA antibodies", Mol. Biochem. Parasitol. 56, 1992, 227-38.

Minenkova et al., "Identification of Tumor-Associated Antigens by Screening Phage-Displayed Human cDNA Libraries With Sera From Tumor Patients", International Journal of Cancer, 2003, 106:534-44.

Okano, et al., Myelin Basic Protein Gene and the Function of Antisense RNA in Its Repression in Myelin-Deficient Mutant Mouse: J. Neurochem 56,560,1991.

Parmley et al., "Expression, Characterization, and Serologic Reactivity of Recombinant Surface Antigen P22 of *Toxoplasma gondii*", 1992, J. Clin. Microbiol. 30, 1127-33.

Prince et al., "Cloning of cDNAs encoding a 28 kilodalton antigen of *Toxoplasma gondii*", Mol. Biochem. Parasitol., 34, 1989, 3-14.

Rabenau et al., "TgM2AP participates in *Toxoplasma gondii* invasion of host cells and is tightly associated with the adhesive protein TgMIC2", Mol. Microbiol., 2001, 41:537-547.

Remington JS et al., "Infectious Diseases of the Fetus and Newborn Infant", W.B. Saunders, Philadelphia, PA, 140-267, 1995.

Robben et al. "Selection and Identification of Dense Granule Antigen GRA3 by *Toxoplasma gondii* Whole Genome Phage Display", 2002, J. Biol. Chem. 277, 17544-47.

Wan et al, "Molecular characterisation of an expressed sequence tag locus of *Toxoplasma gondii* encoding the micronemal protein MIC2", Mol. Biochem.Parasitol., 1997, 84:203-214.

Final Rejection issued by USPTO for U.S. Appl. No. 11/885,951 dated Sep. 30, 2009.

Non-Final Rejection issued by USPTO for U.S. Appl. No. 11/885,951 dated Mar. 12, 2009.

Restriction Requirement issued by USPTO for U.S. Appl. No. 11/885,951 dated Nov. 7, 2008.

Office Communication 94(3) issued by EPO for EP Application No. 06723123.3 dated Apr. 30, 2008.

Office Communication 71(3) issued by EPO for EP Application No. 06723123.3 dated Sep. 2, 2009.

Beghetto, E., et al. Chimeric Antigens of *Toxoplasma gondii*: Toward Standardization of Toxoplasmosis Serodiagnosis Using Recombinant Products. J. Clinical Microbiology, vol. 44, No. 6, pp. 2133-2140 (Jun. 2006).

Ben-Yedidia, T., et al. Towards an Epitope-Based Human Vaccine for Influenza. Human Vaccines, 1:3, pp. 95-101 (May/Jun. 2005).

Rosenberg, C., et al. Induction of partial protection against infection with *Toxoplasma gondii* genotype II by DNA vaccination with recombinant chimeric tachyzoite antigens. Vaccine, 27, pp. 2489-2498 (2009).

Seder, R.A., et al. Vaccines against intracellular infections requiring cellular immunity. Nature, vol. 406, pp. 793-798 (Aug. 17, 2000).

Sorensen, H.P., et al. Soluble expression of recombinant proteins in the cytoplasm of *Escherichia coli*. Microbial Cell Factories, 4:1 (2005).

Decision to grant a European patent issued by the EPO for EP Application No. 06723123.3 dated Mar. 11, 2010.

Interview Summary issued by USPTO for U.S. Appl. No. 11/885,951 dated Dec. 10, 2009.

* cited by examiner

CHIMERIC RECOMBINANT ANTIGENS OF
TOXOPLASMA GONDII

CROSS REFERENCE TO RELATED APPLICATIONS

This application is a continuation in part of International Application PCT/EP2006/001760 filed on Feb. 27, 2006 which, in turn, claims priority to European Application 05005065.7 filed on Mar. 8, 2005, the disclosures of both of which are incorporated herein by reference in their entirety. This application is also related to U.S. patent application Ser. No. 11/885,951 filed on Sep. 6, 2007, which is the national phase of International Application PCT/EP2006/001760 filed on Feb. 27, 2006 which, in turn, claims priority to European Application 05005065.7 filed on Mar. 8, 2005.

FIELD OF THE INVENTION

The invention described herein relates to the technical field of the preparation of diagnostic means not applied directly to the animal or human body. The invention also furnishes compounds, methods for their preparation, methods for their use and compositions containing them, which are suitable for industrial application in the pharmaceutical and diagnostic field, particularly for the detection and diagnosis of *Toxoplasma gondii* infections, as well as for the treatment and prevention of said infections.

BACKGROUND OF THE INVENTION

Early diagnosis is a priority and highly desirable objective in all fields of medicament, particularly because it allows an appreciable improvement in the patient's life and a concomitant saving on the part of health care systems or on the part of the actual patients. In the particular case of the invention described herein, early diagnosis is that of potential or existing *Toxoplasma gondii* infection in pregnant women, with particular concern for the health of the foetus, and in infected subjects, particularly those with impaired immunity.

*Toxoplasma gondii* is an obligate intracellular parasite that infects all mammalian cells, including those of human subjects (McCabe and Remington, *N. Engl. J. Med.* 1988, 318-313-5). Morphologically, the parasite exhibits three distinct forms of infection: tachyzoite (asexual), bradyzoite (in tissue cysts, asexual) and sporozoite (in oocysts, sexual reproduction). Transmission typically occurs through ingestion of undercooked meat harbouring tissue cysts or vegetables contaminated with oocysts shed by cats. Human infection is generally asymptomatic and self-limiting in immunocompetent hosts. In contrast, in subjects with impaired immunity (particularly those affected by AIDS), toxoplasmosis is a severe opportunist infection, which may give rise to encephalitis with very serious outcomes (Luft, B. J., Remington J. S., 1992, *Clin. Infect. Dis.* 15, 211-22). Moreover, contracting primary infection during pregnancy may lead to miscarriages or to severe foetal disease in mammals.

For an extensive overview of the problem of toxoplasmosis the reader is, referred to the specific medical literature.

Diagnosis of *T. gondii* infection is established by isolating the micro-organism in the blood or body fluids, identifying the parasite in tissues, detecting specific nucleotide sequences with PCR, or detecting specific anti-*T. gondii* immunoglobulins produced by the host in response to the infection (Beaman et al., 1995 *Principles and Practice of Infectious Diseases* 4th Ed., Churchill Livingstone Inc., New York, 2455-75; Remington J S et al. 1995, *Infectious Diseases of the Fetus and Newborn Infant*, W. B. Saunders, Philadelphia, Pa., 140-267).

Main challenges for clinicians are the diagnosis of primary *T. gondii* infections in pregnant women and the diagnosis of congenital infection in their newborns/infants. In both cases, to implement suitable therapies in good time and to avoid possible damage to the foetus and newborns/infants, it is very important to establish if the parasitic infection has been contracted before or after conception in pregnant women. Moreover, it is essential determining when the vertical transmission from the mother to the foetus occurred. Finally, for the clinical management of newborns/infants there is an urgent need of a sensitive diagnostic method than can discriminate, early in their life, between infected and uninfected subjects, both born to mothers with primary toxoplasmosis in pregnancy.

Seroconversion during gestation and diagnosis of congenital infection in neonates are generally done by attempting to detect the presence of the various classes of anti-*Toxoplasma* immunoglobulins (IgG, IgM, IgA, avidity of IgG), and to compare the immunological profiles of the mother versus her child. However, the available commercial assays do not provide enough sensitivity and specificity to allow a correct diagnosis of infection in all patients. Therefore the availability of specific, sensitive and innovative diagnostic agents is desirable.

*T. gondii* antigens have long been known and available, first of all as antigen mixtures obtained in various ways (FR 2,226, 468, Mérieux; SU 533376, Veterinary Research Institute; JP 54044016, Nihon Toketsu Kanso), then as subsequent isolations of pure antigens (EP 0 082 745, Mérieux; EP 0 301 961, INSERM, Pasteur; WO 89/5658, Transgene) and their characterization both as proteins, and of their respective genes (WO 89/08700, U. Leland, Dartmouth Coll.; U.S. Pat. No. 4,877,726, Res. Inst. Palo Alto; WO 89/12683, INSERM, Pasteur; EP 0 391 319, Mochida Pharm.; IT 1,196,817, CNR; EP 0 431 541, Behringwerke; WO 92/01067, CNRS; WO 92/02624, U. Flinders; WO 92/11366, Innogenetics, Smithkline Beecham; U.S. Pat. No. 5,215,917, Res. Inst. Palo Alto; WO 92/25689, FR 2702491, INSERM, Pasteur; WO 96/02654, bioMeriéux, Transgene; EP 0 710 724 Akzo; EP 0 724 016, bioMeriéux; EP 0 751 147, Behringwerke; U.S. Pat. No. 5,633,139, Res. Inst. Palo Alto; WO 97/27300, Innogenetics; U.S. Pat. No. 5,665,542, U.S. Pat. No. 5,686,575, Res. Inst. Palo Alto; WO 99/32633, Heska; JP 11225783, Yano; WO 99/61906, Abbott; WO 99/66043, Smithkline Beecham; JP 2000300278, Yano; WO 00/164243, Virsol), and finally, the isolation and characterization of the antigenic regions of *Toxoplasma* gene products (WO 03/080839, Kenton S.r.l.) Numerous studies have found various different antigenic proteins of *T. gondii* and the gene sequences of these have also been determined.

Among the most interesting proteins both for diagnostic and therapeutic purposes, in the form of vaccines, we should mention: the microneme proteins (WO 03/080839, Kenton S.r.l.; Beghetto et al., *The Journal of Infectious Diseases*, 2005, 191:637-645; Beghetto et al., *International Journal for Parasitology*, 2003, 33:163-173); the surface antigens SAG1 (or P30) (WO 89/08700, Stanford University; WO 89712683 Pasteur, INSERM; WO 94/17813, WO 96/02654, Transgene, bioMeriéux; EP 0 724 016, WO 99/61906, U.S. Pat. No. 5,962,654, Harning et al., *Clinical and Diagnostic Laboratory Immunology*, May 1996, 355-357) and SAG2 (or P22) (Parmley et al., 1992, *J. Clin. Microbiol.* 30, 1127-33); the dense granule proteins GRA1 (or P24) (EP 0 301 961, Pasteur, INSERM; WO 89/05658, Transgene, Cesbron-Delauw, et al., 1989 *P.N.A.S. USA* 86, 7537-41), GRA2 (or P28) (WO 93/25689, INSERM, Pasteur; U.S. Pat. Nos. 5,633,139, 5,665,542, 5,686,575, Res. Inst. Palo Alto; Prince et al., *Mol. Biochem. Parasitol.,* 34 3-14), GRA4 (Mevelec et al., *Mol. Biochem. Parasitol.* 56, 227-38), GRA6 (or P32) (FR 2,702, 491, INSERM, Pasteur; Lecordier al., *Mol. Biochem. Parasitol.* 70, 85-94), GRA7 (WO 99/61906, Abbott; Jacobs et al., *Mol. Biochem. Parasitol.* 91, 237-49) and GRA3 (Robben et al. 2002, *J. Biol. Chem.* 277, 17544-47): the rhoptry antigens ROP1 (or P66) (U.S. Pat. No. 5,976,553, U. Leland; EP 0 431 541, Innogenetics) and ROP2 (or P54) (Sharma et al., *J. Immunol.,* 131, 377-83).

As described in the above-mentioned references, the antigens were obtained with recombinant cDNA techniques in expression vectors. For example, for the antigen SAG1, WO 98/08700 uses known expression vectors in phage lambda-gt11. WO 98/12683 uses the same phage and transfects *E. coli* with a proprietary plasmid, or by preparing a special expression cassette, as in WO 96/02654. EP 0 724 016 obtains mimotopes using combinatorial expression libraries of peptides. EP 0 301 961 describes how to obtain excretion-secretion antigens with molecular weights ranging from 20 kDa to 185 kDa. WO 89/05658 describes a protein containing the epitopes of the 24 kDa protein recognized by the antibodies produced against *Toxoplasma* excretion-secretion antigens; this protein is obtained by transfection of cells by means of expression vectors. WO 03/080839 describes a method based on phage-display technology for identifying antigen fragments of *T. gondii* proteins and their use as diagnostic and immunogenic agents. The antigen P28 (GRA2) is described in U.S. Pat. No. 5,633,139 and the method of obtaining it is again implemented through expression in phage lambda-gt11. The antigen P32 (GRA6) is described in patent FR 2,702,491, the antigen ROP1 (P66) in U.S. Pat. No. 5,976, 553, P35 (or GRA8) in EP 0 431 541, WO 99/57295 and WO 99/61906, and lastly P68 in EP 0 431 541.

Yang et al. (Parasitol. Res., 2004, 92: 58-64) describe a chimeric protein containing SAG1 and SAG2 and its use to develop immunity against *T. gondii* in mice.

Chinese Patent 11 94991C discloses a recombinant fusion protein containing two *toxoplasma* antigens (GRA6 and p30). No data are reported to show that assays based on this recombinant fusion protein display the required sensitivity in IgG- and IgM-based tests.

During the last ten years, several studies have reported the use of recombinant antigens for the serological diagnosis of *T. gondii* infection. Nevertheless, although promising none of the assays based on recombinant antigens displayed all the characteristics required to replace the tachyzoite antigen in IgG- and IgM-based tests, indicating that further work is needed before an immunoassay employing recombinant products will be available for clinical purposes.

Thus the main aim of the studies in this filed is to improve the performance of enzyme-linked immunoassays based on recombinant products, thus improving, for example early diagnosis of congenital toxoplasmosis in newborns/infants.

SUMMARY OF THE INVENTION

It has now been found that the combination of antigenic regions of *Toxoplasma gondii* proteins, in the form of recombinant fusion products, retains the antigenic properties of the individual antigen fragments. The corresponding chimeric proteins thus produced can be used for diagnostic and therapeutic purposes.

The use of said chimeric antigens as diagnostic agents and the related diagnostic aids containing them, for example in the form of enzyme-linked immunoassays or kits, constitute a further object of the present invention.

Another object of the present invention are the gene sequences coding for the above-mentioned chimeric antigens, their use as medicaments, particularly for the prevention and therapy of *Toxoplasma gondii* infection, e.g. as gene therapy. The present invention also extends to the gene sequences that hybridize with the sequences of the above-mentioned chimeric antigens in stringent hybridization conditions.

Another object of the present invention is the use of the chimeric antigens as medicaments, particularly in the form of vaccines, which are useful for the prevention and cure of the infection. The vaccines according to the present invention are suitable for use in humans and other animals (particularly pig, cat, sheep).

These and other objects will be illustrated here below in detail, also by means of examples and figures.

DETAILED DESCRIPTION OF THE INVENTION

The main object of the present invention is, therefore, the provision of recombinant chimeric antigens obtained through the fusion of different antigenic regions of *Toxoplasma gondii* gene products, and the use of the recombinant proteins thus obtained for developing selective diagnostic and therapeutic means.

The main advantages of the present invention over the other types of antigens or antigen fragments known in the literature as reported above are the following and are evident when these antigens are used in diagnostic immunoassays on sample sera for detection of the infection:

With respect to the use of the entire *Toxoplasma gondii* antigen, prepared from the parasite as lysed, whole-cell extract, the chimeric recombinant antigens have the advantage of avoiding unspecific reactions due to the presence of other non-proteinaceous material and of providing a better reproducibility. Moreover, some natural protein antigens of the parasite are insoluble and, consequently, are poorly represented in commercial assays employing the lysed, whole-cell extract of *T. gondii*.

With respect to the use of single antigenic regions or single antigen fragments (as described in WO 03/080839), the recombinant chimeric antigens show the advantage of improving the sensitivity of the assays in which they are used. In other words their use decreases or abolishes the occurrence of false negative responses.

A) With respect to the use of a mixture or a collection of single antigenic regions (as also envisaged in WO 03/080839), the advantages are least two. From the point of view of the industrial applicability and production is much easier to produce a single engineered construct containing three or more antigen regions rather than separately produce each single fragment and subsequently assemble them by an economic and reproducible method. Secondly, as already said before, the use of the chimeric recombinant antigens of the invention improves the sensitivity of the assays.

These and other advantages are shown in the Examples section.

In particular the present invention relates to a chimeric recombinant antigen containing the fusion at least three different antigenic regions of *Toxoplasma gondii*, wherein said antigenic regions are B-cell epitopes, which bind to *Toxoplasma gondii*-specific antibodies. Preferably the *Toxo-*

*plasma gondii*-specific antibodies are extracted from sera of subjects who have been infected by *Toxoplasma gondii.*

More particularly the present invention covers a chimeric antigen, wherein the three different antigenic regions have an amino acid sequence selected from the group consisting of: SEQ ID NO: 2, SEQ ID NO: 4, SEQ ID NO: 6, SEQ ID NO: 8, SEQ ID NO: 10, SEQ ID NO: 12, SEQ ID NO: 33, SEQ ID NO: 34, SEQ ID NO: 35, SEQ ID NO: 36, SEQ ID NO: 37, SEQ ID NO: 38, SEQ ID NO: 39, SEQ ID NO:40, SEQ ID NO: 41 and SEQ ID NO: 42. Preferred sequences in the above group are SEQ ID NO: 2, SEQ ID NO: 4, SEQ ID NO: 6, SEQ ID NO: 8, SEQ ID NO: 10 and SEQ ID NO: 12.

For example the chimeric antigen of the invention comprises the amino acid sequence of SEQ ID NO: 28 or the amino acid sequence of SEQ ID NO: 30 or the amino acid sequence of SEQ ID NO: 32.

The chimeric antigens of the present invention may be engineered using known methods. The fusions may be direct (the C-terminus of one amino acid sequence is linked to the N-terminal of the other through a simple covalent bond) or they may employ a flexible linker domain, such as the hinge region of human IgG, or polypeptide linkers consisting of small amino acids such as glycine, serine, threonine or alanine, at various lengths and combinations. For example the linker may be a polyglycine repeat interrupted by serine or threonine at a certain interval. Preferably, the linker is composed by three glycine residues and two serine residues, giving the aminoacid sequence Ser-Gly-Gly-Gly-Ser (SGGGS linker) (SEQ ID 47).

Additionally, the chimeric antigens of the invention may be tagged by His-His-His-His-His-His (His6), to allow rapid purification by metal-chelate chromatography, and/or by epitopes to which antibodies are available, to allow for detection on western blots, immunoprecipitation, or activity depletion/blocking in bioassays.

Another object of the present invention is a nucleotide sequence coding for the chimeric antigen as defined above. According to a preferred embodiment of the invention such nucleotide sequence comprises at least three different nucleotide sequences selected from the group consisting of: SEQ ID NO: 1, SEQ ID NO: 3, SEQ ID NO: 5, SEQ ID NO: 7, SEQ ID NO: 9 and SEQ ID NO: 11. According to a more preferred embodiment, such nucleotide sequence comprises the nucleotide sequence of SEQ ID NO: 27 or the nucleotide sequence of SEQ ID NO: 29 or the nucleotide sequence of SEQ ID NO: 31.

Also included in the scope of the present invention are nucleotide sequences that hybridizes with any sequence described above under stringent hybridization conditions, as well the corresponding chimeric recombinant antigen encoded by such hybridized nucleotide sequence.

The chimeric antigens of the present invention may be prepared by cloning and expression in a prokaryotic or eukaryotic expression system, using the appropriate expression vectors. Any method known in the art can be employed.

For example the DNA molecules coding for the antigens of the invention are inserted into appropriately constructed expression vectors by techniques well known in the art (see Sambrook et al, 1989). Such vectors are another object of the present invention.

In order to be capable of expressing the desired protein (in this case the chimeric antigens), an expression vector should comprise also specific nucleotide sequences containing transcriptional and translational regulatory information linked to the DNA coding the desired protein in such a way as to permit gene expression and production of the protein. First in order for the gene to be transcribed, it must be preceded by a promoter recognizable by RNA polymerase, to which the polymerase binds and thus initiates the transcription process. There are a variety of such promoters in use, which work with different efficiencies (strong and weak promoters).

For eukaryotic hosts, different transcriptional and translational regulatory sequences may be employed, depending on the nature of the host. They may be derived form viral sources, such as adenovirus, bovine papilloma virus, Simian virus or the like, where the regulatory signals are associated with a particular gene, which has a high level of expression. Examples are the TK promoter of the Herpes virus, the SV40 early promoter, the yeast gal4 gene promoter, etc. Transcriptional initiation regulatory signals may be selected which allow for repression and activation, so that expression of the genes can be modulated. All these hosts are a further object of the present invention.

Nucleic acid molecules which encode the chimeric antigens of the invention may be ligated to a heterologous sequence so that the combined nucleic acid molecule encodes a fusion protein. Such combined nucleic acid molecules are included within the embodiments of the invention. For example, they may be joined to the DNA coding for a protein which allows purification of the chimeric antigen by only one step of affinity chromatography. This joined/fused protein may be for example Glutathione Sulpho Transferase (GST) to generate fusion products at the carboxy terminus of GST protein. The corresponding recombinant proteins expressed in the cytoplasm of transformed *E. coli* cells may be purified by affinity chromatography using a Glutathione-Sepharose resin.

The DNA molecule comprising the nucleotide sequence coding for the chimeric molecule of the invention is inserted into vector(s), having the operably linked transcriptional and translational regulatory signals, which is capable of integrating the desired gene sequences into the host cell. The cells which have been stably transformed by the introduced DNA can be selected by also introducing one or more markers which allow for selection of host cells which contain the expression vector. The marker may also provide for phototrophy to an auxotropic host, biocide resistance, e.g. antibiotics, or heavy metals such as copper, or the like. The selectable marker gene can either be directly linked to the DNA gene sequences to be expressed, or introduced into the same cell by co-transfection. Additional elements may also be needed for optimal synthesis of proteins of the invention.

Factors of importance in selecting a particular plasmid or viral vector include: the ease with which recipient cells, that contain the vector may be recognized and selected form those recipient cells which do not contain the vector; the number of copies of the vector which are desired in a particular host; and whether it is desirable to be able to "shuttle" the vector between host cells of different species.

Once the vector(s) or DNA sequence containing the construct(s) has been prepared for expression the DNA construct(s) mat be introduced into an appropriate host cell by any of a variety of suitable means: transformation, transfection, conjugation, protoplast fusion, electroporation, calcium phosphate-precipitation, direct microinjection, etc.

Host cells may be either prokaryotic or eukaryotic. Example of eukaryotic hosts are mammalian cells, such as human, monkey, mouse, and Chinese hamster ovary (CHO) cells. Expression in these host cells provides post-translational modifications to protein molecules, including correct folding or glycosylation at correct sites. Also yeast cells can carry out post-translational peptide modifications including glycosylation. A number of recombinant DNA strategies exist which utilize strong promoter sequences and high copy number of plasmids which can be utilized for production of the desired proteins in yeast. Yeast recognizes leader sequences on cloned mammalian gene products and secretes peptides bearing leader sequences (i.e., pre-peptides). Example of prokaryotic hosts are bacteria, such as *Escherichia coli*.

After the introduction of the vector(s), the host cells are grown in a selective medium, which selects for the growth of vector-containing cells. Expression of the cloned gene sequence(s) results in the production of the desired proteins.

Purification of the recombinant antigens is carried out by any one of the methods known for this purpose, i.e. any conventional procedure involving extraction, precipitation, chromatography, electrophoresis, or the like. A further purification procedure that may be used in preference for purifying the antigens of the invention is affinity chromatography using monoclonal antibodies which bind the target protein and which are produced and immobilized on a gel matrix contained within a column. Impure preparations containing the recombinant protein are passed through the column. The antigens will be bound to the column by the specific antibody while the impurities will pass through. After washing, the antigen is eluted from the gel by a change in pH or ionic strength.

Another aspect of the present invention is the process for the recombinant production of the chimeric antigen as described above, comprising culturing the host cell transformed with the vector containing the nucleotide sequence of the invention and isolating the desired product.

A further object of the present invention is a DNA molecule comprising the DNA sequence coding for the above fusion protein, as well as nucleotide sequences substantially the same.

"Nucleotide sequences substantially the same" includes all other nucleic acid sequences which, by virtue of the degeneracy of the genetic code, also code for the given amino acid sequence.

Another object of the present invention is a nucleotide sequence which hybridizes to the complement of the nucleotide sequence coding for the chimeric antigen of the invention under highly stringent or moderately stringent conditions, as long as the antigen obtained maintains the same biological activity, i.e. ability to bind to antibodies against the parasite.

The term "hybridization" as used here refers to the association of two nucleic acid molecules with one another by hydrogen bonding. Typically, one molecule will be fixed to a solid support and the other will be free in solution. Then, the two molecules may be placed in contact with one another under conditions that favour hydrogen bonding. Factors that affect this bonding include: the type and volume of solvent; reaction temperature; time of hybridization; agitation; agents to block the non-specific attachment of the liquid phase molecule to the solid support (Denhardt's reagent or BLOTTO); the concentration of the molecules; use of compounds to increase the rate of association of molecules (dextran sulphate or polyethyleneglycol); and the stringency of the washing conditions following hybridization.

Stringency conditions are a function of the temperature used in the hybridization experiment, the molarity of the monovalent cations and the percentage of formamide in the hybridization solution. To determine the degree of stringency involved with any given set of conditions, one first uses the equation of Meinkoth et al. (1984) for determining the stability of hybrids of 100% identity expressed as melting temperature Tm of the DNA-DNA hybrid: $Tm=81.5° C.+16.6 (Log M)+0.41 (\% GC)-0.61 (\% form)-500/L$, where M is the molarity of monovalent cations, % GC is the percentage of G and C nucleotides in the DNA, % form is the percentage of formamide in the hybridization solution, and L is the length of the hybrid in base pairs. For each 1° C. that the Tm is reduced from that calculated for a 100% identity hybrid, the amount of mismatch permitted is increased by about 1%. Thus, if the Tm used for any given hybridization experiment at the specified salt and formamide concentrations is 10° C. below the Tm calculated for a 100% hybrid according to equation of Meinkoth, hybridization will occur even if there is up to about 10% mismatch.

As used herein, highly stringent conditions are those which are tolerant of up to about 15% sequence divergence, while moderately stringent conditions are those which are tolerant of up to about 20% sequence divergence. Without limitation, examples of highly stringent (12-15° C. below the calculated Tm of the hybrid) and moderately (15-20° C. below the calculated Tm of the hybrid) conditions use a wash solution of 2×SSC (standard saline citrate) and 0.5% SDS at the appropriate temperature below the calculated Tm of the hybrid. The ultimate stringency of the conditions is primarily due to the washing conditions, particularly if the hybridization conditions used are those which allow less stable hybrids to form along with stable hybrids. The wash conditions at higher stringency then remove the less stable hybrids. A common hybridization condition that can be used with the highly stringent to moderately stringent wash conditions described above is hybridization in a solution of 6×SSC (or 6×SSPE), 5× Denhardt's reagent, 0.5% SDS, 100 µg/ml denatured, fragmented salmon sperm DNA at a temperature approximately 20° C. to 25° C. below the Tm. If mixed probes are used, it is preferable to use tetramethyl ammonium chloride (TMAC) instead of SSC (Ausubel, 1987-1998).

The term "nucleic acid molecule" also includes analogues of DNA and RNA, such as those containing modified backbones.

The nucleic acid molecules of the invention also include antisense molecules that are partially complementary to nucleic acid molecules encoding antigens of the present invention and that therefore hybridize to the encoding nucleic acid molecules (hybridization). Such antisense molecules, such as oligonucleotides, can be designed to recognise, specifically bind to and prevent transcription of a target nucleic acid encoding a polypeptide of the invention, as will be known by those of ordinary skill in the art (see, for example, Cohen, J. S., Trends in Pharm. Sci., 10,435 (1989), Okano, J. Neurochem. 56, 560 (1.991); O'Connor, J. Neurochem 56,560 (1991); Lee et al., Nucleic Acids Res 6,3073 (1979); Cooney et al., Science 241, 456 (1988); Dervan et al., Science 251, 1360 (1991).

According to the terminology used herein, a composition containing a compound [X] is "substantially free of" impurities [herein, Y] when at least 85% by weight of the total X+Y in the composition is X. Preferably, X comprises at least about 90% by weight of the total of X+Y in the composition, more preferably at least about 95%, 98% or even 99% by weight.

Another aspect of the invention is the use of chimeric antigens described above as medicaments. In particular, one of the main objects of the invention is use of chimeric antigens as active ingredients for the preparation of medicaments for the prevention or treatment of *Toxoplasma gondii* infections.

In the case of gene therapy another object of the invention is the use of the nucleotide sequences coding for the antigens of the invention as medicaments, in particular for the preparation of medicaments useful for the treatment and prevention of *Toxoplasma gondii* infections.

The pharmaceutical compositions should preferably comprise a therapeutically effective amount of the chimeric antigens of the invention or the corresponding nucleotide sequence. Chimeric antigens of the invention may thus act as vaccines for the prevention or the treatment of *Toxoplasma gondii* infection.

For the therapeutic application, where the preparation of medicaments or vaccines comes within the framework of general knowledge for further reference the reader is again referred to the patent literature cited in the present description and, particularly, to Beghetto et al., *The Journal of Infectious Diseases,* 2005, 191:637-645.

The term "therapeutically effective amount" as used herein refers to an amount of a therapeutic agent needed to treat, ameliorate, or prevent a targeted disease or condition, or to exhibit a detectable therapeutic or preventative effect. For any compound, the therapeutically effective dose can be estimated initially either in cell culture assays, for example, of neoplastic cells, or in animal models, usually mice, rabbits, dogs, or pigs.

The animal model may also be used to determine the appropriate concentration range and route of administration. Such information can then be used to determine useful doses and routes for administration in humans.

The precise effective amount for a human subject will depend upon the severity of the disease state, general health of the subject, age, weight, and gender of the subject, diet, time and frequency of administration, drug combination (s), reaction sensitivities, and tolerance/response to therapy. This amount can be determined, by routine experimentation and is within the judgement of the clinician. Generally, an effective dose will be from 0.01 mg/kg to 50 mg/kg, preferably 0.05 mg/kg to 10 mg/kg. Compositions may be administered individually to a patient or may be administered in combination with other agents, drugs or hormones.

A pharmaceutical composition may also contain a pharmaceutically acceptable carrier, for administration of a therapeutic agent. Such carriers include antibodies and other polypeptides, genes and other therapeutic agents such as liposomes, provided that the carrier does not itself induce the production of antibodies harmful to the individual receiving the composition, and which may be administered without undue toxicity.

Suitable carriers may be large, slowly metabolised macromolecules such as proteins, polysaccharides, polylactic acids, polyglycolic acids, polymeric amino acids, amino acid copolymers and inactive virus particles.

Pharmaceutically acceptable salts can be used therein, for example, mineral acid salts such as hydrochlorides, hydrobromides, phosphates, sulphates, and the like; and the salts of organic acids such as acetates, propionates, malonates, benzoates, and the like. A thorough discussion of pharmaceutically acceptable carriers is available in Remington's Pharmaceutical Sciences (Mack Pub. Co., N.J. 1991).

Pharmaceutically acceptable carriers in therapeutic compositions may additionally contain liquids such as water, saline, glycerol and ethanol. Additionally, auxiliary substances, such as wetting or emulsifying agents, pH buffering substances, and the like, may be present in such compositions. Such carriers enable the pharmaceutical compositions to be formulated as tablets, pills, dragees, capsules, liquids, gels, syrups, slurries, suspensions, and the like, for ingestion by the patient.

Once formulated, the compositions of the invention can be administered directly to the subject. The subjects to be treated can be animals; in particular, human subjects can be treated.

The pharmaceutical compositions utilised in this invention may be administered by any number of routes including, but not limited to, oral, intravenous, intramuscular, intra-arterial, intramedullary, intrathecal, intraventricular, transdermal ortranscutaneous applications (for example, see WO98/20734), subcutaneous, intraperitoneal, intranasal, enteral, topical, sublingual, intravaginal or rectal means. Gene guns or hyposprays may also be used to administer the pharmaceutical compositions of the invention. Typically, the therapeutic compositions may be prepared as injectables, either as liquid solutions or suspensions; solid forms suitable for solution in, or suspension in, liquid vehicles prior to injection may also be prepared.

Direct delivery of the compositions will generally be accomplished by injection, subcutaneously, intraperitoneally, intravenously or intramuscularly, or delivered to the interstitial space of a tissue. The compositions can also be administered into a lesion.

Dosage treatment may be a single dose schedule or a multiple dose schedule.

The method of treating a mammal suffering from *Toxoplasma-gondii* infection, comprising administering a therapeutically effective amount of the vaccine as described above represents one of the aspects of the present invention.

A further object of the present invention is the use of chimeric antigens as described above as active agents for the diagnosis of *Toxoplasma gondii* infections, in particular for the diagnosis of the time of infection.

Also the kits for the diagnosis of *Toxoplasma gondii* infection, containing at least one chimeric antigen according are part of the present invention. Such kits amy be useful for the diagnosis of an acute and/or chronic *Toxoplasma gondii* infection.

The chimeric antigen of the invention may be employed in virtually any assay format that employs a known antigen to detect antibodies. A common feature of all of these assays is that the antigen is contacted with the body component suspected of containing antibodies under conditions that permit the antigen to bind to any such antibody present in the component. Such conditions will typically be physiologic temperature, pH and ionic strength using an excess of antigen. The incubation of the antigen with the specimen is followed by detection of immune complexes comprised of the antigen.

Design of the immunoassays is subject to a great deal of variation, and many formats are known in the art. Protocols may, for example, use solid supports, or immunoprecipitation. Most assays involve the use of labeled antibody or polypeptide; the labels may be, for example, enzymatic, fluorescent, chemiluminescent, radioactive, or dye molecules. Assays which amplify the signals from the immune complex are also known; examples of which are assays which utilize biotin and avidin, and enzyme-labeled and mediated immunoassays, such as ELISA assays.

The immunoassay may be, without limitation, in a heterogenous or in a homogeneous format, and of a standard or competitive type. In a heterogeneous format, the polypeptide is typically bound to a solid matrix or support to facilitate separation of the sample from the polypeptide after incubation.

Examples of solid supports that can be used are nitrocellulose (e.g., in membrane or microtiter well form), polyvinyl chloride (e.g., in sheets or microtiter wells), polystyrene latex (e.g., in beads or microtiter plates, polyvinylidine fluoride (known as Immulon™), diazotized paper, nylon membranes, activated beads, and Protein A beads. For example, Dynatech Immulon™1 or Immulon™2 microtiter plates or 0.25 inch polystyrene beads (Precision Plastic Ball) can be used in the heterogeneous format. The solid support containing the antigenic polypeptides is typically washed after separating it from the test sample, and prior to detection of bound antibodies.

Both standard and competitive formats are known in the art.

In a homogeneous format, the test sample is incubated with the combination of antigens in solution. For example, it may be under conditions that will precipitate any antigen-antibody complexes which are formed. Both standard and competitive formats for these assays are known in the art.

In a standard format, the amount of antibodies forming the antibody-antigen complex is directly monitored. This may be accomplished by determining whether labeled anti-xenogenic (e.g., anti-human) antibodies which recognize an epitope on anti-*Toxoplasma gondii* antibodies will bind due to complex formation. In a competitive format, the amount of antibodies in the sample is deduced by monitoring the competitive effect on the binding of a known amount of labeled antibody (or other competing ligand) in the complex.

Complexes formed comprising anti-*Toxoplasma gondii* antibody (or, in the case of competitive assays, the amount of competing antibody) are detected by any of a number of known techniques, depending on the format. For example, unlabeled antibodies in the complex may be detected using a conjugate of antixenogeneic Ig complexed with a label, (e.g., an enzyme label).

In an immunoprecipitation or agglutination assay format the reaction between the chimeric antigens and the antibody forms a network that precipitates from the solution or suspension and forms a visible layer or film of precipitate. If no anti-*Toxoplasma gondii* antibody is present in the test specimen, no visible precipitate is formed.

The chimeric antigens of the invention will typically be packaged in the form of a kit for use in these immunoassays. The kit will normally contain in separate containers the combination of antigens (either already bound to a solid matrix or separate with reagents for binding them to the matrix), control antibody formulations (positive and/or negative), labeled antibody when the assay format requires same and signal generating reagents (e.g., enzyme substrate) if the label does not generate a signal directly. Instructions (e.g., written, tape, VCR, CD-ROM, etc.) for carrying out the assay usually will be included in the kit.

The diagnostic kits, which are the object of the present invention, are therefore known to the expert in the field. By way of an example, the reader is referred to the patent literature cited above, to which may be added U.S. Pat. No. 6,265,176, WO 01/63283, and WO 03/080839 as further references.

The invention will now be illustrated in greater detail by means of examples and figures.

The DNA sequences of clones Tx-2.a, Tx-1.16, Tx-4.18, Tx-15.11, Tx-1.11 and Tx-11.b, respectively encoding for protein fragments of the *T. gondii* genes MIC2, M1C3, SAG1, GRA3, GRA7 and M2AP were used for the construction of GST-EC2, GST-EC3 and GST-EC4 fusion proteins.

Figure 1:
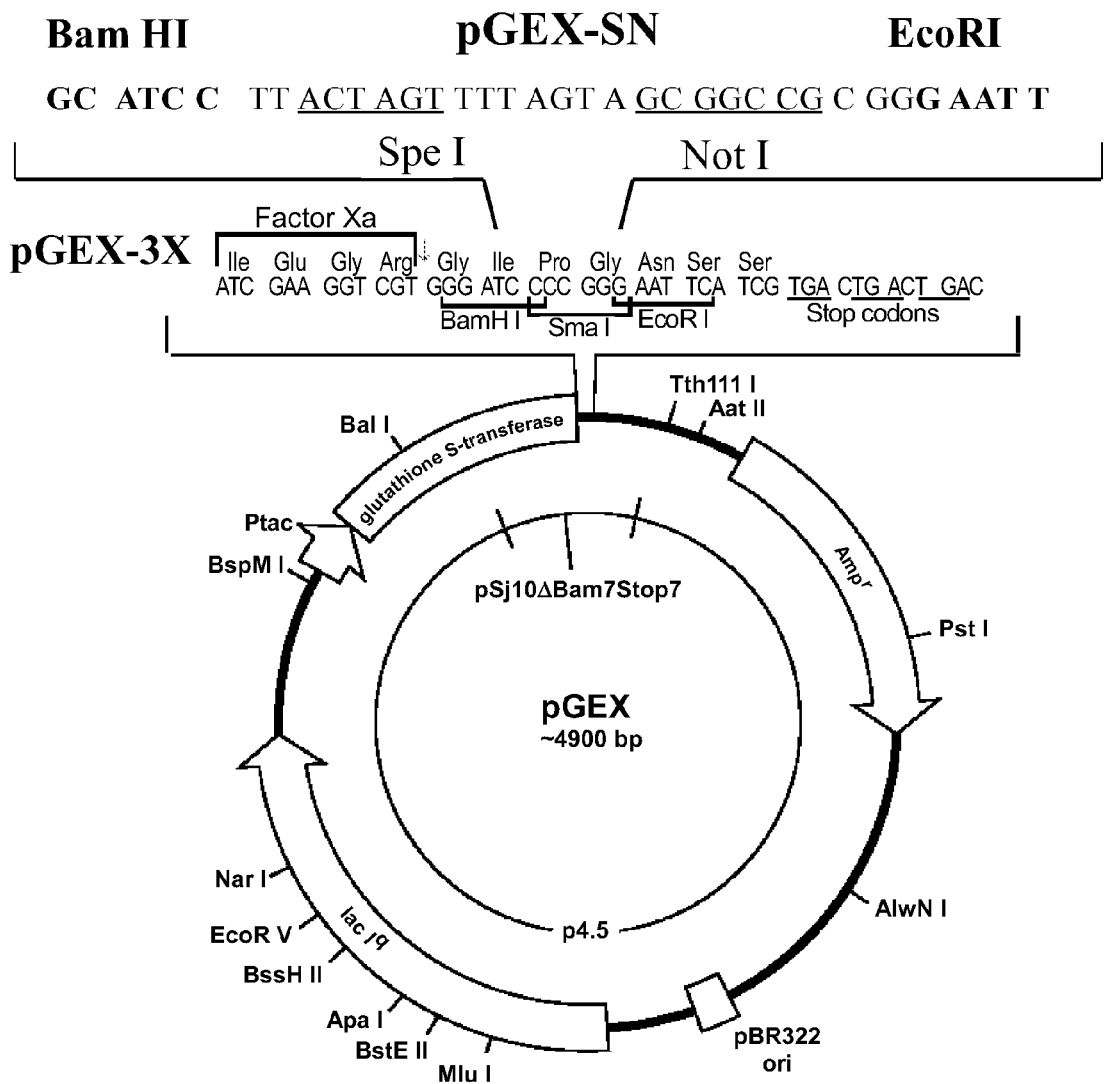
FIG. 1. Plasmid map of the bacterial expression vector pGEX-SN.
Figure 2:
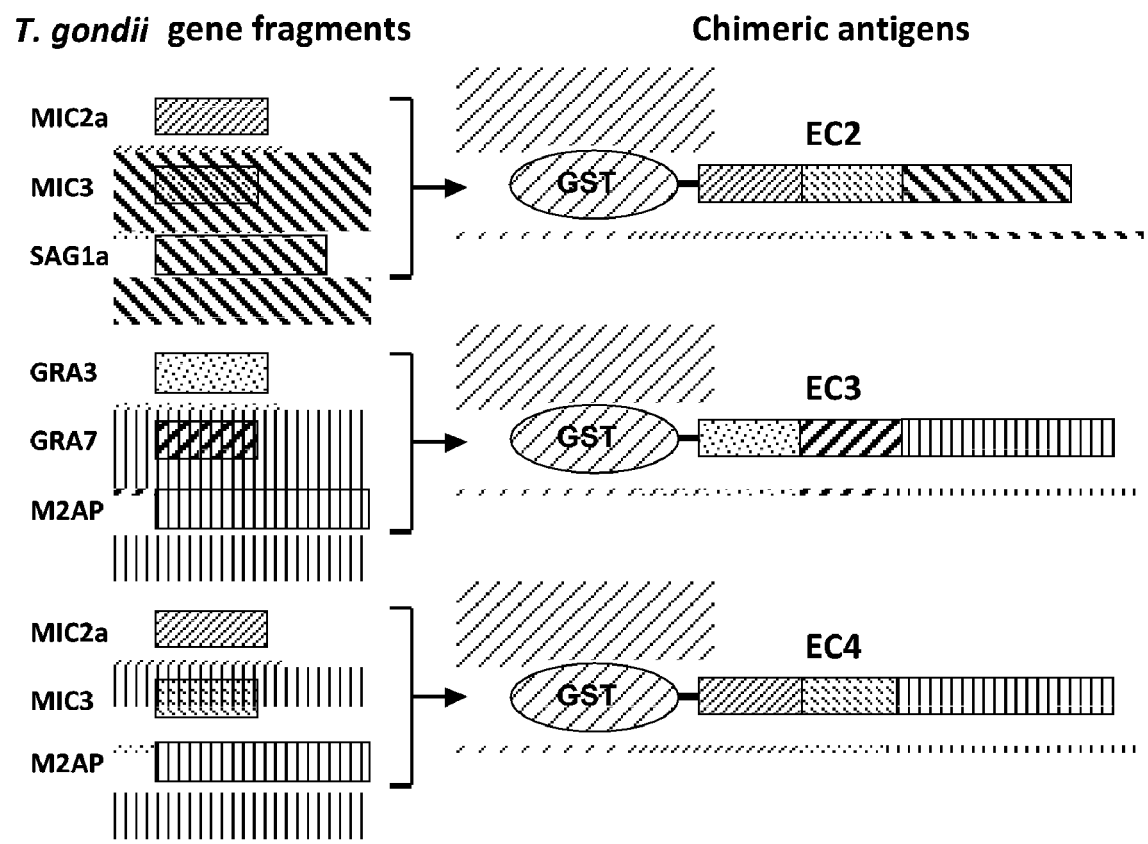
FIG. 2. Schematic representation of the chimeric antigens.
Figure 3:
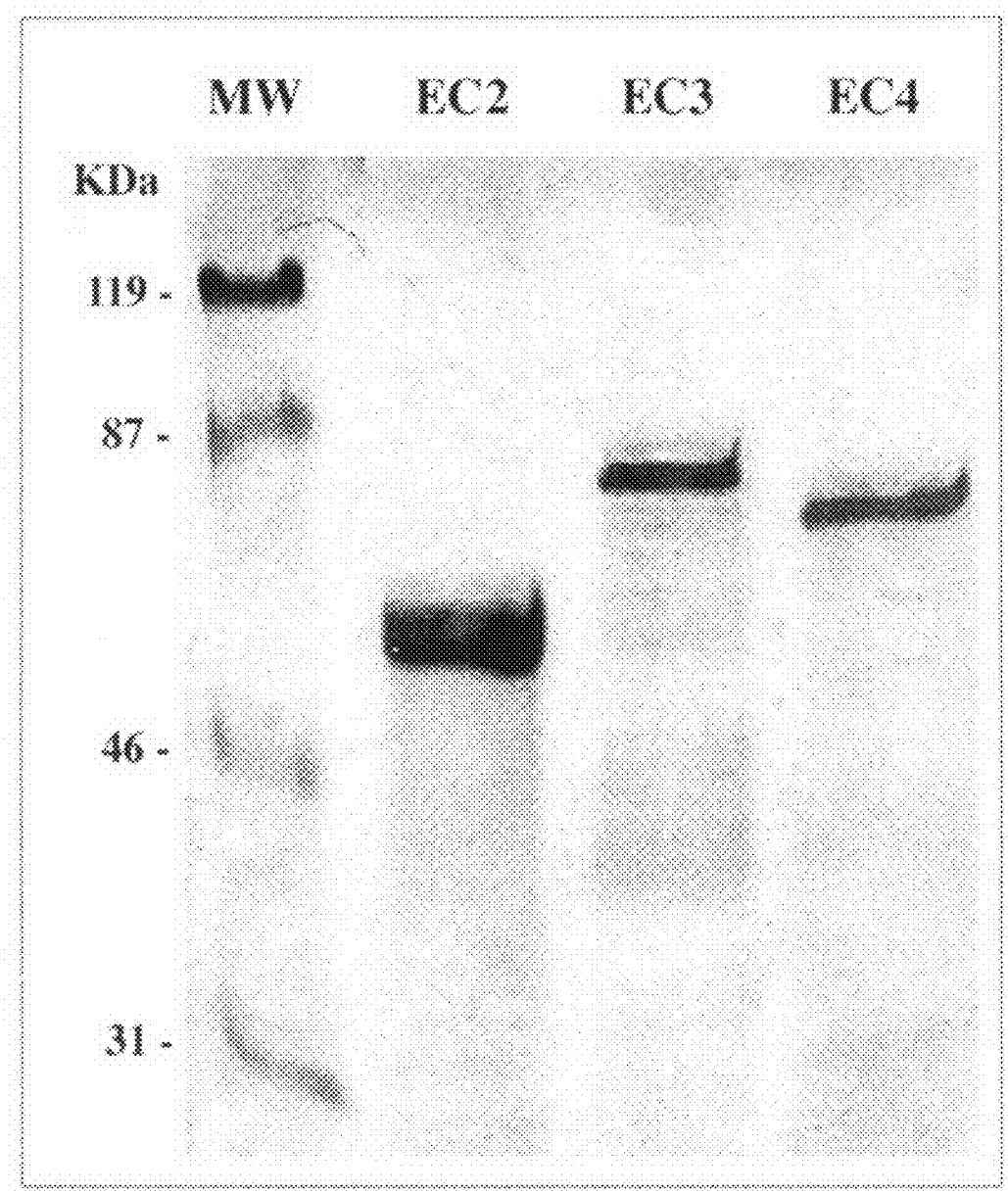

FIG. 3. Expression of *T. gondii* chimeric antigens in *E. coli* cells.

SDS-PAGE analysis of purified GST-EC2, GST-EC3 and GST-EC4 fusion proteins. The recombinant proteins were subjected to electrophoresis (0.003 mg/lane) on 12% acrylamide gel. MW, molecular weight markers.

Figure 4:
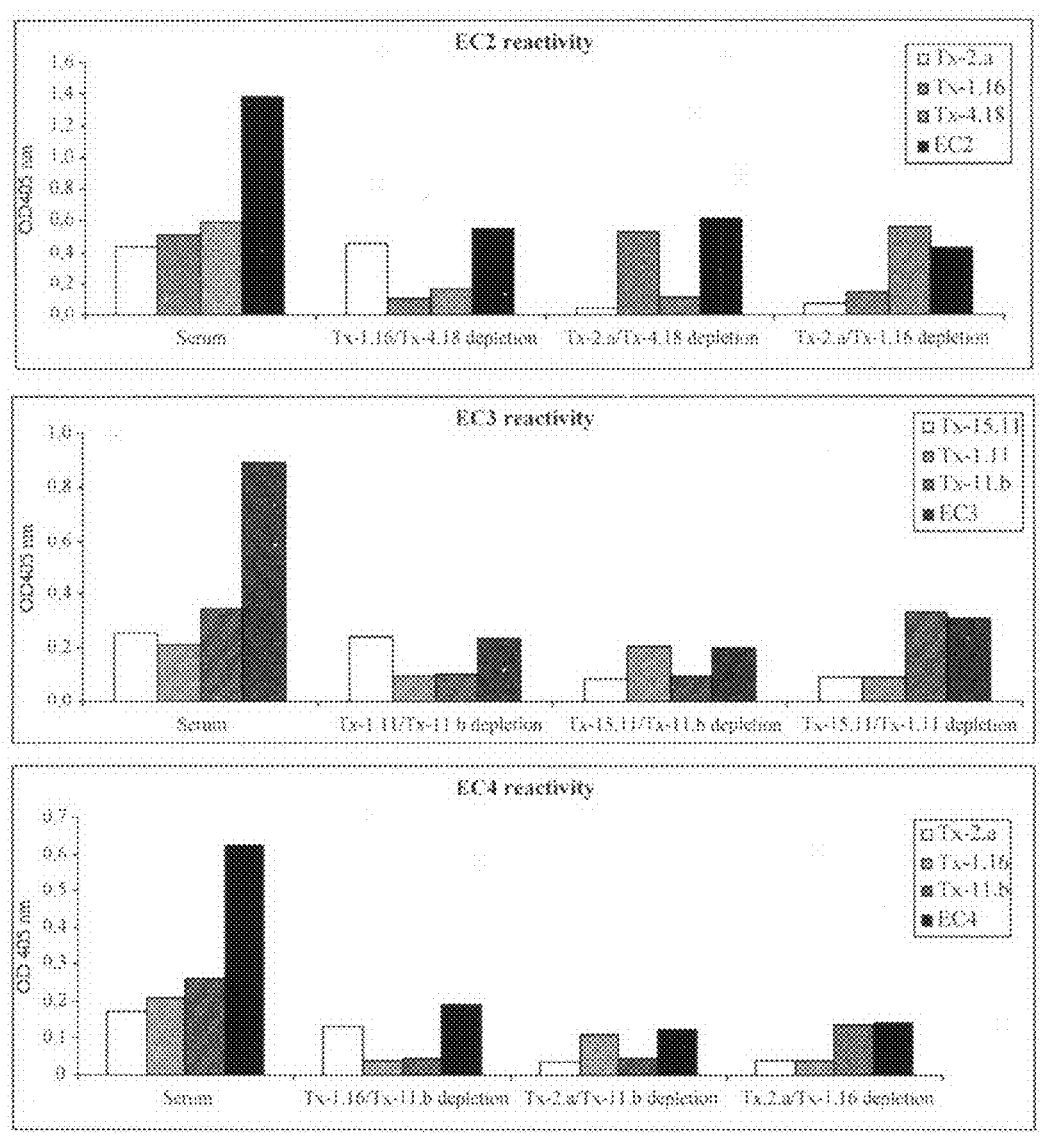

FIG. 4. Antigenic properties of individual protein fragments within the chimeric antigens.

Immunoreactivity of individual Tx-2.a, Tx-1.16, Tx-4.18, Tx-15.11, Tx-1.11 and Tx-11.b antigen fragments, and of EC2, EC3 and EC4 chimeric antigens with serum samples from *T. gondii* infected individuals. Sera were used either as whole speciments (serum) or after depletion of specific antibodies against combinations of antigen fragments (Tx-1.16/Tx-4.18 depletion, Tx-2.a/Tx-4.18 depletion, etc.).

Figure 5:
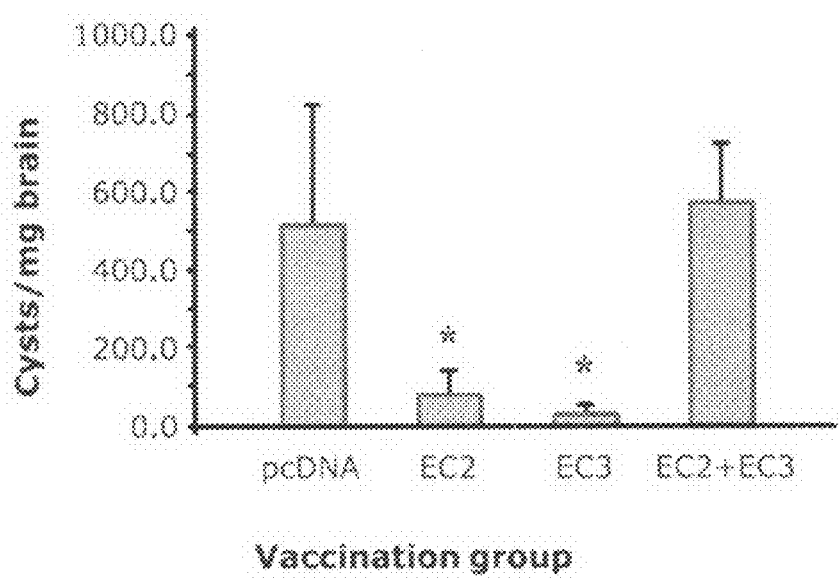
Figure 5:
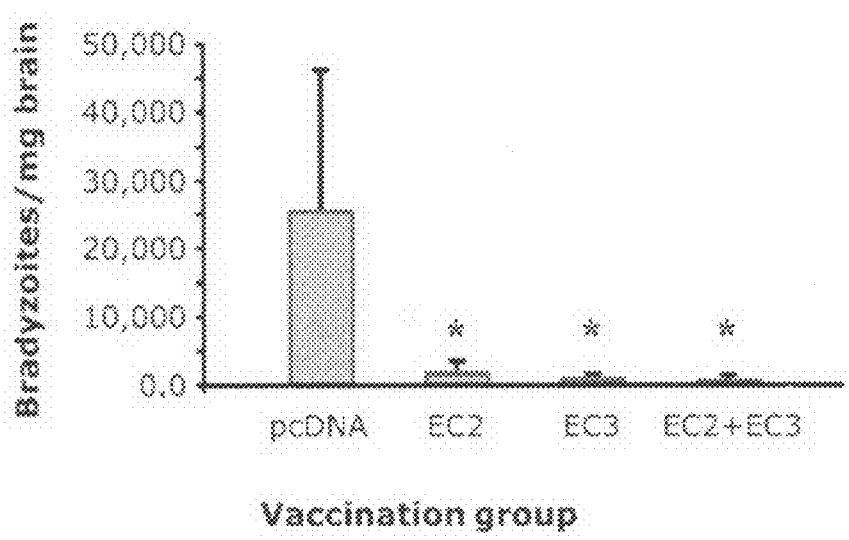

FIG. 5. Protective effect of DNA immunization in BALB/c mice orally infected with *T. gondii* tissue cysts.

The efficacy of DNA vaccination was evaluated by microscopy on (A) cyst formation and by PCR on (B) bradyzoite load in the mice brains. Cyst numbers were counted in whole brain homogenates. Data represent the average brain cyst number or bradyzoites with Standard Error from pcDNA3 control-vaccinated mice (n=7), and pcDNA-EC3 vaccinated mice (n=8). *P<0.05 student-t test.

Figure 6:
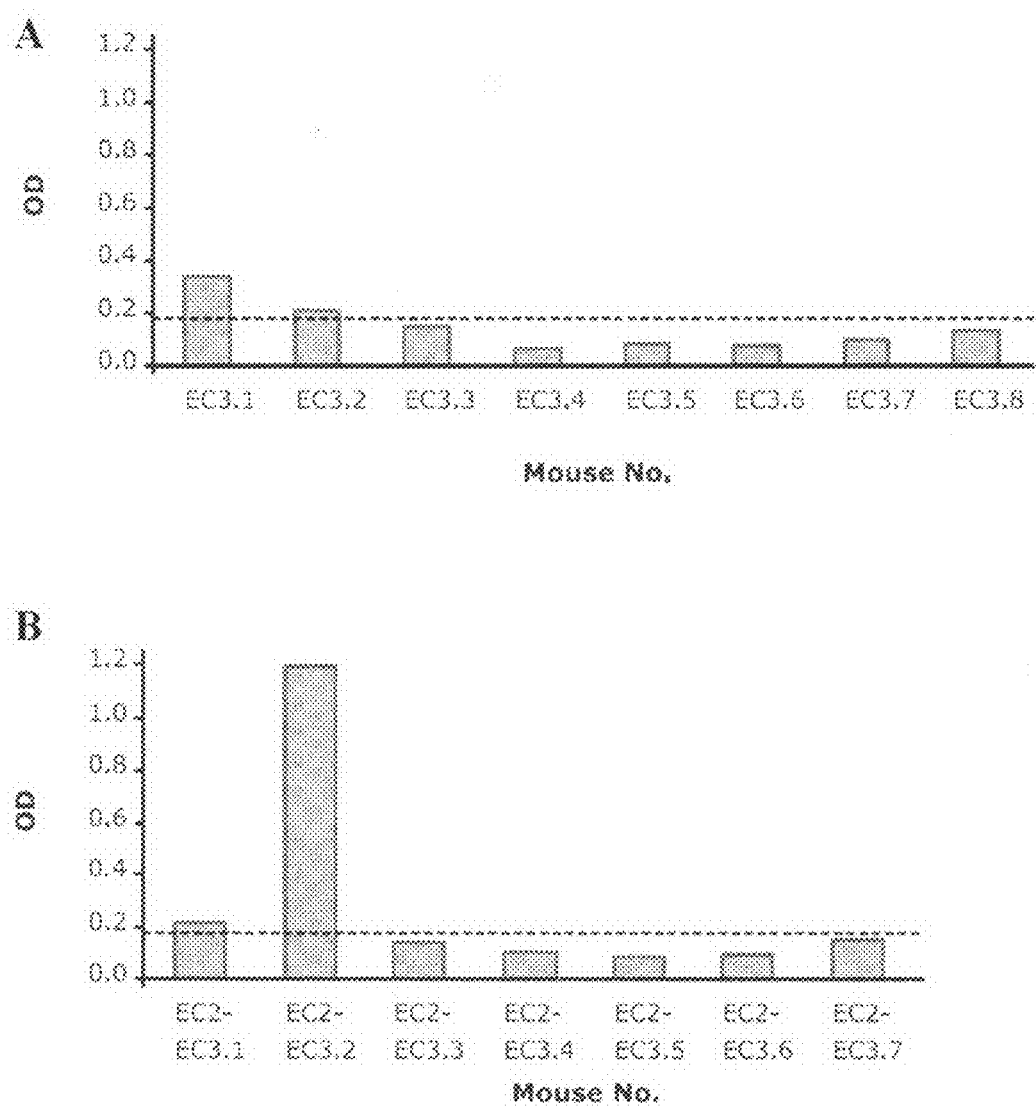

FIG. 6. Total production of IgG antibodies against EC3 in vaccinated mice

Sera from BALB/c mice immunized with pcDNA-EC3 (n=8), and with the pcDNA-EC2/pcDNA-EC3 combination (n=7) were analyzed by ELISA, after the last immunization, against GST-EC3 using anti-mouse-IgG antibodies. Cutoff value (dashed lines) was determined as the average reading obtained by assaying sera from mice immunized with control pcDNA3.1 vector (n=7). Cutoff=0.182.

EXAMPLES

The following Table 1 gives, by way of examples, the DNA sequences used for the construction of recombinant *Toxoplasma gondii* chimeric antigens:

TABLE 1

| Name | Sequence | Identification | Classification |
|---|---|---|---|
| Tx-15.11 (SEQ ID 1) | GCTGCCTTGGGAGGCCTTGCGGCGGATC AGCCTGAAAATCATCAGGCTCTTGCAGA ACCAGTTACGGGTGTGGGGAAGCAGGA GTGTCCCCCGTCAACGAAGCTGGTGAGT CATACAGTTCTGCAACTTCGGGTGTCCA AGAAGCTACCGCCCCAGGTGCAGTGCTC CTGGACGCAATCGATGCCGAGTCGGATA AGGTGGACAATCAGGCGGAGGGAGGTGA GCGTATGAAGAAGGTCGAAGAGGAGTTG TCGTTATTGAGGCGGGAATTATATGATC GCACAGATCGCCCTGGT | GRA 3 | Dense granule protein |

TABLE 1-continued

| Name | Sequence | Identification | Classification |
|---|---|---|---|
| Tx-1.11 (SEQ ID 3) | CAGTTCGCTACCGCGGCCACCGCGTCAG ATGACGAACTGATGAGTCGAATCCGAAA TTCTGACTTTTTCGATGGTCAAGCACCC GTTGACAGTCTCAGACCGACGAACGCCG GTGTCGACTCGAAAGGGACCGACGATCA CCTCACCACCAGCATGGATAAGGCATCT GTAGAGAGTCAGCTTCCGAGAAGAGAGC CATTGGAGACGGAGCCAGATGAACAAGA AGAAGTTCAT | GRA 7 | Dense granule protein |
| Tx-1.16 (SEQ ID 5) | AGGAGGACTGGATGTCATGCCTTCAGGG AGAACTGCAGCCCTGGTAGATGTATTGA TGACGCCTCGCATGAGAATGGCTACACC TGCGAGTGCCCCACAGGGTACTCACGTG AGGTGACTTCCAAGGCGGAGGAGTCGTG TGTGGAAGGAGTCGAAGTCACGCTGGCT GAGAAATGCGAGAAGGAATTCGGCATCA GCGCGTCATCCTGCAAATGCGAT | MIC 3 | Microneme protein |
| Tx-4.18 (SEQ ID 7) | CCATCGGTCGTCAATAATGTCGCAAGGT GCTCCTACGGTGCAGACAGCACTCTTGG TCCTGTCAAGTTGTCTGCGGAAGGACCC ACTACAATGACCCTCGTGTGCGGGAAAG ATGGAGTCAAAGTTCCTCAAGACAACAA TCAGTACTGTTCCGGGACGACGCTGACT GGTTGCAACGAGAAATCGTTCAAAGATA TTTTGCCAAAATTAACTGAGAACCCGTG GCAGGGTAACGCTTCGAGTGATAAGGGT GCCACGCTAACGATCAAGAAGGAAGCAT TCCAGCCGAGTCAAAAAGCGTCATTAT TGGATGCACAGGGGGATCGCCTGAGAAG CATCACTGTACCGTGAAACTGGAGTTTG CCGGGGCTGCAGGGTCAGCAAAATCGGC T | SAG 1 | Surface protein |
| Tx-2.a (SEQ ID 9) | CCCCAGGATGCCATTTGCTCGGATTGGT CCGCATGGAGCCCCTGCAGTGTATCCTG CGGTGACGGAAGCCAAATCAGGACGCGA ACTGAGGTTTCTGCTCCGCAACCTGGAA CACCAACATGTCCGGACTGCCCTGCGCC CATGGGAAGGACTTGCGTGGAACAAGGC GGACTTGMGAAATCCGTGAATGCAGTGC GGGGGTATGTGCTGTTGACGCTGGATGT GGCGTCTGGGTT | MIC2 | Microneme protein |
| Tx-11.b (SEQ ID 11) | AACGAACCGGTGGCCCTAGCTCAGCTCA GCACATTCCTCGAGCTCGTCGAGGTGCC ATGTAACTCTGTTCATGTTCAGGGGGTG ATGACCCCGAATCAAATGGTCAAAGTGA CTGGTGCAGGATGGGATAATGGCGTTCT CGAGTTCTATGTCACGAGGCCAACGAAG ACAGGCGGGGACACAAGCCGAAGCCATC TTGCGTCGATCATGTGTTATTCCAAGGA CATTGACGGCGTGCCGTCAGACAAAGCG GGAAAGTGCTTTCTGAAGAACTTTTCTG GTGAAGACTCGTCGGAAATAGACGAAAA AGAAGTATCTCTACCCATCAAGAGCCAC AACGATGCGTTCATGTTCGTTTGTTCTT CAAATGATGGATCCGCACTCCAGTGTGA TGTTTTCGCCCTTGATAACACCAACTCT AGCGACGGGTGGAAAGTGAATACCGTGG ATCTTGGCGTCAGCGTTAGTCCGGATTT GGCATTCGGACTCACTGCAGATGGGGTC AAGGTGAAGAAGTTGTACGCAAGCAGCG GCCTGACAGCGATCAACGACGACCCTTC CTTGGGGTGCAAGGCTCCTCCCCATTCT CCGCCGGCCGGAGAGGAACCGAGTTTGC CGTCGCCTGAAAACAGCGGGTCTGCAAC ACCAGCGGAAGAAAGTCCGTCTGAGTCT GAATCT | M2AP | Microneme protein |

The sequence Tx-15.11 constitutes a fragment of the gene GRA3 (Bermudes et al., *Mol. Biochem. Parasitol.*, 1994, 68:247-257). Said clone has the amino acid sequence AALG-GLAADQPENHQALAEPVTGVGEAGVSPVNEAGES-YSSATSGVQEATA PGAVLLDAIDAESDKVDNQAEG-GERMKKVEEELSLLRRELYDRTDRPG (SEQ ID 2) and its use in chimeric antigens is covered by the present invention.

The sequence Tx-1.11 constitutes a fragment of the antigen GRA7 (Bonhomme et al., *J. Histochem. Cytochem.*, 1998, 46:1411-1421). Said clone has the amino acid sequence ATAATASDDELMSRIRNSDFFDGQAPVD-SLRPTNAGVDSKGTDDHLTTSMDK ASVESQLPRRE-PLETEPDEQEEVHF (SEQ ID 4) and its use in chimeric antigens is covered by the present invention.

The sequence Tx-1.16 constitutes a fragment of the MIC3 gene (Garcia-Réguet et al., *Cellular Microbiol.*, 2000, 2:353-364). Said clone has the amino acid sequence RRT-GCHAFRENCSPGRCIDDASHENGYT-CECPTGYSREVTSKAEESCVEGV EVTLAEKCEKEFGISASSCKCD (SEQ ID 6) and its use in chimeric antigens is covered by the present invention.

The sequence Tx-4.18 constitutes a fragment of the antigen SAG1 (Burg et al., *J. Immunol.*, 1988, 141:3584-3591). Said clone has the amino acid sequence PSWNNVARCSYGAD-STLGPVKLSAEGPTT-MTLVCGKDGVKVPQDNNQYCS GTTLTGCNEKSFK-DILPKLTENPWQGNASSDKGATLTIKKEAFPAESKS-VIIGC TGGSPEKHHCTVKLEFAGMGSAKSA (SEQ ID 8) and its use, in chimeric antigens is covered by the present invention.

The sequence Tx-2.a represents a fragment of the MIC2 gene (Wan et al, *Mol. Biochem. Parasitol.*, 1997, 84:203-214). Said clone has the amino acid sequence PQDAICSD-WSAWSPCSVSCGDGSQIR-TRTEVSAPQPGTPTCPDCPAPMGRT CVEQGGLEEIRECSAGVCAVDAGCGVWV (SEQ ID 10) and its use in chimeric antigens is covered by the present invention.

The sequence Tx-11.b represents a distinct fragment of the M2AP gene (Rabenau et al., *Mol. Microbiol.*, 2001, 41:537-547). Said clone has the amino acid sequence NEPVALAQL-STFLELVEVPCNSVHVQGVMTPNQMVKVTGAGW-DNGVLEFYV TRPTKTGGDTSRSHLASIMCYSKDID-GVPSDKAGKCFLKNFSGEDSSEIDEKE VSLPIKSHN-DAFMFVCSSNDGSALQCDVFALDNTNSSDGWKVN-TVDLGVSVS PDLAFGLTADGVKVKKLYASSGLTAIN-DDPSLGCKAPPHSPPAGEEPSLPSPE NSGSATPAEE-SPSESES (SEQ ID 12) and its use in chimeric antigens is covered by the present invention.

Construction of Chimeric Antigens

EC2 protein product is a chimeric molecule containing the DNA sequences Tx-2.a, Tx-1.16 and Tx-4.18. SEQ ID 9 was used as template for DNA amplification of clone Tx-2.a by using oligonucleotides K551 (5'-GGACTAGTCGGCTC-CCCCAGGATGCC-3') (SEQ ID 13) and K553 (5'-CATC-CAGTCCTGCTACCGCCACCAGACCA-GACGCCACATCC AGC-3') (SEQ ID 14). The oligonucleotide K553 contains a sequence encoding for the linker SGGGS (SEQ ID 47), which joins the sequences Tx-2.a and Tx-1.16. PCR condition was 30" at 94° C., 30" at 50° C. and 60" at 72° C. for 20 cycles.

SEQ ID 5 was used as template for DNA of clone Tx-1.16 by using oligonucleotides K552 (5'-GTGGCGTCTG-GTCTGGTGGCGGTAGCAG GACTGGATGTCATGCC-3') (SEQ ID 15) and K555 (5'-TGACGACCGAGCTAC CGCCACCAGAGTTATCGCATTTGCAGGATG-3') (SEQ ID 16). The oligonucleotide K555 contains a sequence encoding for the linker SGGGS (SEQ ID 47), which joins the sequences Tx-1.16 and Tx-4.18. PCR condition was 30" at 94° C., 30" at 50° C. and 60" at 72° C. for 20 cycles.

SEQ ID 7 was used as template for DNA amplification of clone Tx-4.18 by using oligonucleotides K554 (5'-ATGC-GATAACTCTGGTGGCGG TAGCTCGGTCGT-CAATAATGTCGC-3') (SEQ ID 17) and K556 (5'-CCGCG-GCC GCTAGCCGATTTTGCTGACCCTG-3') (SEQ ID 18) PCR condition was 30" at 94° C., 30" at 50° C. and 60" at 72° C. for 20 cycles.

The PCR products were purified by means of the "Qiagen Purification Kit" (Qiagen, Calif., USA). 25 ng of DNA amplification products of SEQ ID 9 and SEQ ID 5 were mixed together and used as templates in PCR reaction by using oligonucleotides K551 and K555. PCR condition was 30" at 94° C., 30" at 50° C. and 60" at 72° C. for 20 cycles. 25 ng of the resulting DNA amplification was purified with "Qiagen Purification Kit" (Qiagen, Calif., USA) and then mixed with 25 ng of DNA amplification product of SEQ ID 4. Finally, the DNA mixture was used as template for DNA amplification by using oligonucleotides K551 and K556, following PCR condition of 30" at 94° C., 30" at 50° C. and 90" at 72° C. for 20 cycles.

EC3 protein product is a chimeric molecule containing the DNA sequences Tx-15.11, Tx-1.11 and Tx-11.b.

SEQ ID 1 was used as template for DNA amplification of clone Tx-15.11 by using oligonucleotides K563 (5'-GGAC-TAGTCGGCTGG CTGCCTTGGGAGGCCTTG-3') (SEQ ID 19) and K565 (5'-GCCGCGGTAGCACTACCG CCAC-CAGACAAACCAGGGCGATCTGTG-3') (SEQ ID 20). The oligonucleotide K565 contains a sequence encoding for the linker SGGGS (SEQ ID 47), which joins the sequences Tx-15.11 and Tx-1.11. The PCR protocol was 30" at 94° C., 30" at 48° C. and 60" at 72° C. for 20 cycles.

SEQ ID 3 was used as template for DNA amplification of clone Tx-1.11 by using oligonucleotides K564 (5'-GCCCTG-GTTTGTCTGGTGGCGGTAG TGCTACCGCGGCCAC-CGCG-3') (SEQ ID 21) and K567 (5'-CCGGTTCGTTAC-TACCG CCACCAGAGAAATGAACTTCTTCTTGTTC-3') (SEQ ID 22). The oligonucleotide K567 contains a sequence encoding for the linker SGGGS (SEQ ID 47), which joins the sequences Tx-1.11 and Tx-11.b. The PCR protocol was 30" at 94° C., 30" at 48° C. and 60" at 72° C. for 20 cycles.

SEQ ID 11 was used as template for DNA amplification of clone Tx-11.b by using oligonucleotides K566 (5'-GAAGT-TCATTTCTCTGGTGGCG GTAGTAACGAACCGGTG-GCCCTAG-3') (SEQ ID 23) and K568 (5'-CCGCGGCCGC AGATTCAGACTCAGACGGAC-3') (SEQ ID 24). The PCR protocol was 30" at 94° C., 30" at 45° C. and 60" at 72° C. for 20 cycles.

The PCR products were purified by means of the "Qiagen Purification Kit" (Qiagen, Calif., USA). 25 ng of DNA amplification products of SEQ ID 1 and SEQ ID 3 were mixed together and used as templates in PCR reaction by using oligonucleotides K563 and K567. The PCR protocol was 30" at 94° C., 30" at 45° C. and 60" at 72° C. for 30 cycles. 25 ng of the resulting DNA amplification was purified and then mixed with 25 ng of DNA amplification product of SEQ ID 11. Finally, the DNA mixture was used as template for DNA amplification by using oligonucleotides K563 and K568, following PCR condition of 30" at 94° C., 30" at 45° C. and 180" at 72° C. for 30 cycles.

EC4 protein product is a chimeric molecule containing the DNA sequences Tx-2.a, Tx-1.16 and Tx-11.b.

SEQ ID 9 was used as template for DNA amplification of clone Tx-2.a using oligonucleotides K551 and K553.

SEQ ID 5 was used as template for DNA amplification of clone Tx-1.16 by using oligonucleotides K552 and K572 (5'-CGTTACTACCGC CACCAGAGTTATCGCATTTG-CAGGATGA-3') (SEQ ID 25). The oligonucleotide K572 contains a sequence encoding for the linker SGGGS (SEQ ID 47), which joins the sequences Tx-1.16 and Tx-11.b.

SEQ ID 11 was used as template for DNA amplification of clone Tx-11.b by using oligonucleotides K571 (5'-TAACTCTGGTGGCGGTAGT AACGAACCGGTGGC-CCTAGC-3') (SEQ ID 26) and K568.

The PCR products were purified as by using "Qiagen Purification Kit" (Qiagen, Calif., USA). 25 ng of DNA amplification products of SEQ ID 9 and SEQ ID 5 were mixed together and used as templates in PCR reaction by using oligonucleotides K551 and K572. 25 ng of the resulting DNA amplification was purified and then mixed with 25 ng of DNA amplification product of SEQ ID 11. Finally, the DNA mixture was used as template for DNA amplification by using oligonucleotides K551 and K568. PCR conditions for the construction of EC4 were the same that those used for EC2 and EC3 constructs.

The following Table 2 gives, by way of examples, the DNA sequences of the EC2, EC3 and EC4 chimeric antigens:

TABLE 2

| Name | Sequence |
| --- | --- |
| EC2 SEQ ID 27 | ACTAGTCGGCTCCCCCAGGATGCCATTTGCTCGGATTGGTC CGCATGGAGCCCTGCAGTGTATCCTGCGGTGACGGAAGCC AAATCAGGACGCGAACTGAGGTTTCTGCTCCGCAACCTGGA ACACCAACATGTCCGGACTGCCCTGCCCCATGGGAAGGAC TTGCGTGGAACAAGGCGGACTTGAAGAAATCCGTGAATGCA GTGCGGGGTATGTGCTGTTGACGCTGGATGTGGCGTCTGG TCTGGTGGCGGTAGCAGGACTGGATGTCATGCCTTCAGGGA GAACTGCAGCCCTGGTAGATGTATTGATGACGCCTCGCATG AGAATGGCTACACCTGCGAGTGCCCCACAGGGTACTCACGT GAGGTGACTTCCAAGGCGGAGGAGTCGTGTGTGGAAGGAGT CGAAGTCACGCTGGCTGAGAAATGCGAGAAGGAATTCGGCA TCAGCGCGTCATCCTGCAAATGCGATAACTCTGGTGGCGGT AGCTCGGTCGTCAATAATGTCGCAAGGTGCTCCTACGGTGC AGACAGCACTCTTGGTCCTGTCAAGTTGTCTGCGGAAGGAC CCACTACAATGACCCTCGTGTGCGGGAAAGATGGAGTCAAA GTTCCTCAAGACAACAATCAGTACTGTTCCGGGACGACGCT GACTGGTTGCAACGAGMATCGTTCAAAGATATTTTGCCAAA ATTAACTGAGAACCCGTGGCAGGGTAACGCTTCGAGTGATA AGGGTGCCACGCTAACGATCAAGAAGGMGCATTTCCAGCCG AGTCAAAAAGCGTCATTATTGGATGCACAGGGGATCGCCT GAGAAGCATCACTGTACCGTGAAACTGGAGTTTGCCGGGGC TGCAGGGTCAGCAAAATCGGCTAGCGGCCGC |
| EC3 SEQ ID 29 | ACTAGTCGGCTGGCTGCCTTGGGAGGCCTTGCGGATCAGCC TGAAAATCATCAGGCTCTTGCAGAACCAGTTACGGGTGTGG GGGAAGCAGGAGTGTCCCCCGTCAACGAAGCTGGTGAGTCA TACAGTTCTGCAACTTCGGGTGTCCAAGAAGCTACCGCCCC AGGTGCAGTGCTTCTGGACGCAATCGATGCCGAGTCGGATA AGGTGGACAATCAGGCGGAGGGAGGTGAGCGTATGAAGAAG GTCGAAGAGGAGTTGTCGTTATTGAGGCGGGAATTATATGA TCGCACAGATCGCCCTGGTTTGTCTGGTGGCGGTAGTGCTA CCGCGGCCACCGCGTCAGATGACGAACTGATGAGTCGAATC CGAAATTCTGACTTTTTCGATGGTCAAGCACCCGTTGACAG TCTCAGACCGACGAACGCCGGTGTCGACTCGAAAGGGACCG ACGATCACCTCACCACCAGCATGGATAAGGCATCTGTAGAG AGTCAGCTTCCGAGAAGAGAGCCATTGGAGACGGAGCCAGA TGAACAAGAAGAAGTTCATTTCTCTGGTGGCGGTAGTAACG AACCGGTGGCCCTAGCTCAGCTCAGCACATTCCTCGAGCTC GTCGAGGTGCCATGTAACTCTGTTCATGTTCAGGGGGTGAT GACCCCGAATCAAATGGTCAAAGTGACTGGTGCAGGATGGG ATAATGGCGTTCTCGAGTTCTATGTCACGAGGCCAACGAAG GATCATACAGGCGGGGACACAAGCCGAAGCCATCTTGCGTC GTGTTATTCCAAGGACATTGACGGCGTGCCGTCAGACAAAG CGGGAAAGTGCTTTCTGAAGAACTTTTCTGGTGAAGACTCG TCGGAAATAGACGAAAAGAAGTATCTCTACCCATCAAGAG |

TABLE 2-continued

| Name | Sequence |
| --- | --- |
| | CCACAACGATGCGTTCATGTTCGTTTGTTCTTCAAATGATG GATCCGCACTCCAGTGTGATGTTTTCGCCCTTGATAACACC AACTCTAGCGACGGGTGGAAAGTGAATACCGTGGATCTTGG CGTCAGCGTTAGTCCGGATTTGGCATTCGGACTCACTGCAG ATGGGGTCAAGGTGAAGAAGTTGTACGCAAGCAGCGGCCTG ACAGCGATCAACGACGACCCTTCCTTGGGGTGCAAGGCTCC TCCCCATTCTCCGCCGGCCGGAGAGGAACCGAGTTTGCCGT CGCCTGAAAACAGCGGGTCTGCAACACCAGCGGAAGAAAGT CCGTCTGAGTCTGAATCTGCGGCCGCGG |
| EC4 SEQ ID 31 | ACTAGTCGGCTCCCCCAGGATGCCATTTGCTCGGATTGGTC CGCATGGAGCCCTGCAGTGTATCCTGCGGTGACGGAAGCC AAATCAGGACGCGAACTGAGGTTTCTGCTCCGCAACCTGGA ACACCAACATGTCCGGACTGCCCCGCGCCCATGGGAAGGAC TTGCGTGGAACAAGGCGGACTTGAAGAAATCCGTGAATGCA GTGCGGGGTATGTGCTGTTGACGCTGGATGTGGCGTCTGG TCTGGTGGCGGTAGCAGGACTGGATGTCATGCCTTCAGGGA GAACTGCCGCCCTGGTAGATGTATTGATGACGCCTCGCATG AGAATGGCTACACCTGCGAGTGCCCCACATGGTACTCACGT GAGGTGACTTCCAAGGCGGAGGAGTCGTGTGTGGAAGGAGT CGAAGTCACGCTGGCTGAGAAATGCGAGAAGGAATTCGGCA TCAGCGCGTCCTCCTGCAAATGCGATAACTCTGGTGGCGGT AGTAACGAACCGGTGGCCCTAGCTCAGCTCAGCACATTCCT CGAGCTCGTCGAGGTGCCATGTAACTCTGTTCATGTTCAGG GGGTGATGACCCCGAATCAAATGGTCAAAGTGACTGGTGCA GGATGGGATAATGGCGTTCTCGAGTTCTATGTCACGAGGCC AACGAAGACAGGCGGGGACACAAGCCGAAGCCACCTTGCGT CGATCATGTGTTATTCCAAGGACATTGACGGCGTGCCGTCA GACAAAGCGGGAAAGTGCTTTTTGAAGAACTTTTCTGGTGA AGACTCGTCGGAAATAGACGAAAAGAAGTATCTCTACCCA TCAAGAGCCACAACGATGCGTTCATGTTCGTTTGTTCTTCA AATGATGGATCCGCACTCCAGTGTGATGTTTTCGCCCTTGA TAACACCAACTCTAGCGACGGGTGGAAAGTGAATACCGTGG ATCTTGACGTCAGCGTTAGTCCGGATTTGGCATTCGGACTC ACTGCAGATGGGGTCAAGGTGAAGAAGTTGTACGCAAGCAG CGGCCTGACAGCGATCAACGACGACCCTTCCTTGGGGTGCA AGGCTCCTCCCCATTCTCCGCCGGCCGGAGAGGAACCGAGT TTGCCGTCGCCTGAAAACAGCGGGTCTGCAACACCAGCGGA AGAAAGTCCGTCTGAGTCTGAATCTGCGGCCGCGG |

The chimeric protein EC2 has the amino acid sequence TSRLPQDAICSDWSAWSPCSVSCGDGSQIRTRTEVS-APQPGTPTCPDCPAP MGRTCVEQGGLEEIRECSAGV-CAVDAGCGVWSGGGSRTGCHAFRENCSPG RCID-DASHENGYTCECPTGYSREVTSKAEESCVEGVEV-TLAEKCEKEFGISAS SCKCDNSGGGSSWNNVARC-SYGADSTLGPVKLSAEGPTTMTLVCGKDGVKVPQ-DNNQYCSGTTLTGCNEKSFKDILPKLTENPWQGN-ASSDKGATLTIKKEAF PAESKSVIIGCTGGSPEKHH-CTVKLEFAGMGSAKSASGR (SEQ ID 28) and its use as recombinant antigen, containing multiple *Toxoplasma gondii* protein fragments, is covered by the present invention.

The chimeric protein EC3 has, the amino acid sequence TSRLMLGGLADQPENHQALAEPVTGVGEAGVSPV-NEAGESYSSATSGVQE ATAPGAVLLDAIDAESbKVD-NQAEGGERMKKVEEELSLLRRELYDRTDRPGLSGG-GSATMTASDDELMSRIRNSDFFDGQAPVDSLRPTN-AGVDSKGTDDHLT TSMDKASVESQLPRREPLETEPD-EQEEVHFSGGGSNEPVALAQLSTFLELVE VPCNSVH-VQGVMTPNQMVKVTGAGWDNGVLEFYVTRPTKT-GGDTSRSHLA SIMCYSKDIDGVPSDKAGKCFLKNFS-GEDSSEIDEKEVSLPIKSHNDAFMFVCS SNDGSALQ-CDVFALDNTNSSDGWKVNTVDLGVSVSPDLAFGL-TADGVKVKKL YASSGLTAINDDPSLGCKAPPHSPPA-GEEPSLPSPENSGSATPAEESPSESES AAA (SEQ ID 30) and its use as recombinant antigen, containing multiple *Toxoplasma gondii* protein fragments, is covered by the present invention.

The chimeric protein EC4 has the amino acid sequence TSRLPQDAICSDWSAWSPCSVSCGDGSQIRTRTEVS- APQPGTPTCPDCPAP MGRTCVEQGGLEEIRECSAGV-
CAVDAGCGVWSGGGSRTGCHAFRENCRPG RCIDDA-
SHENGYTCECPTWYSREVTSKAEESCVEGVEVTLA-
EKCEKEFGISAS SCKCDNSGGGSNEPVALAQLSTFL-
ELVEVPCNSVHVQGVMTPNQMVKVTGA GWDNGV-
LEFYVTRPTKTGGDTSRSHLASIMCYSKDIDGVPSD-
KAGKCFLKNF SGEDSSEIDEKEVSLPIKSHNDAFM-
FVCSSNDGSALQCDVFALDNTNSSDGW KVNTVD-
LDVSVSPDLAFGLTADGVKVKKLYASSGLTAINDDPS-
LGCKAPPHSP PAGEEPSLPSPENSGSATPAEESPSES-
ESAAA (SEQ ID 32) and its use as recombinant antigen, containing multiple *Toxoplasma gondii* protein fragments, is covered by the present invention.

Construction of DNA Vectors Directing the Expression of Chimeric Antigens as Fusion Products with TABLE 3-continued

| Serum sample | IgG levels (IU/ml) | Tx-15.11 | Tx-1.11 | Tx-1.16 | Tx-4.18 | Tx-2.a | Tx-11.b | EC2 | EC3 | EC4 |
|---|---|---|---|---|---|---|---|---|---|---|
| T6 | 35 | 1.2 | 0.8 | 1.0 | 1.3 | 0.9 | 1.4 | 1.4 | 5.7 | 1.7 |
| T7 | 58 | 1.0 | 1.3 | 0.6 | 2.3 | 1.2 | 1.0 | 4.6 | 5.1 | 1.2 |
| T8 | 101 | 2.5 | 0.9 | 2.5 | 2.8 | 11.2 | 2.9 | 17.0 | 4.8 | 30.9 |
| T9 | 88 | 16.2 | 5.9 | 2.4 | 2.7 | 6.8 | 6.7 | 9.4 | 27.4 | 29.9 |
| T10 | 188 | 1.7 | 1.2 | 4.4 | 3.1 | 1.7 | 1.3 | 4.4 | 3.6 | 3.3 |
| T11 | 530 | 28.9 | 12.7 | 12.1 | 31.4 | 32.1 | 31.2 | 32.1 | 42.6 | 41.5 |
| T12 | 89 | 0.9 | nd | 4.8 | nd | 1.2 | 0.5 | 1.7 | 2.4 | 2.1 |
| T13 | 1095 | 8.6 | 2.3 | 3.4 | 5.9 | nd | nd | 31.7 | 23.4 | 20.3 |
| T14 | 248 | 12.6 | 4.3 | 2.1 | 0.9 | nd | nd | 7.4 | 14.6 | 9.2 |
| T15 | 155 | 17.5 | 1.0 | 2.8 | 3.4 | nd | nd | 6.7 | 20.1 | 13.0 |
| T16 | 427 | 4.5 | 3.9 | 5.0 | 2.7 | nd | nd | 17.4 | 37.9 | 18.9 |
| T17 | 236 | 12.1 | 4.8 | 6.1 | 3.7 | nd | nd | 22.0 | 33.9 | 12.7 |
| T18 | 46 | 2.1 | 2.0 | 2.6 | 2.2 | nd | nd | 1.9 | 5.4 | 1.4 |
| T19 | 247 | 2.3 | 2.5 | 3.6 | 0.5 | nd | nd | 3.7 | 3.9 | 2.3 |
| T20 | 100 | nd | nd | nd | nd | 7.5 | 1.4 | 13.1 | 5.2 | 14.6 |
| T21 | 27 | 2.6 | 0.6 | 4.1 | 1.0 | nd | nd | 3.1 | 4.8 | 5.5 |
| T22 | >300 | 28.6 | 5.1 | 4.6 | 19.9 | nd | nd | 14.5 | 14.8 | 7.4 |
| T23 | 92 | 1.7 | 1.1 | 1.3 | 0.8 | 0.7 | 0.8 | 6.9 | 4.5 | 6.4 |
| T24 | 68 | 0.5 | 2.1 | 2.0 | 2.6 | 1.3 | 1.3 | 2.5 | 6.6 | 1.4 |
| T25 | 63 | 2.4 | 2.4 | 5.5 | 6.8 | 8.8 | 7.7 | 13.8 | 16.6 | 32.9 |
| T26 | 299 | 12.1 | 10.0 | 6.5 | 4.6 | nd | nd | 10.0 | 13.5 | 6.0 |
| T27 | 108 | 3.4 | 4.0 | 5.7 | 3.0 | nd | nd | 4.8 | 6.2 | 3.1 |
| T28 | 68 | 1.7 | 2.7 | 3.3 | 2.1 | 2.0 | 2.3 | 6.4 | 6.9 | 7.7 |
| T29 | >300 | 1.0 | 1.1 | 2.8 | 1.2 | 4.0 | 6.3 | 9.1 | 13.7 | 23.5 |
| T30 | 114 | 1.8 | 2.8 | 19.3 | 3.8 | 3.9 | 2.0 | 13.0 | 13.3 | 13.6 |
| T31 | 35 | 3.2 | 1.2 | 3.5 | 0.9 | 1.5 | 1.0 | 3.6 | 6.3 | 5.7 |
| T32 | 300 | 4.8 | 16.0 | 17.3 | 20.9 | nd | nd | 31.6 | 33.1 | 8.4 |
| T33 | 123 | 5.6 | 2.6 | 3.3 | 4.5 | 20.4 | 2.8 | 25.8 | 21.0 | 36.6 |
| T34 | 60 | nd | nd | nd | nd | 6.2 | 4.2 | 9.1 | 7.7 | 9.3 |
| T35 | 155 | 0.7 | 2.4 | 0.5 | 2.3 | 1.8 | 1.1 | 7.3 | 10.4 | 9.5 |
| T36 | 45 | 0.3 | 1.6 | 1.1 | 0.8 | 1.2 | 0.9 | 3.2 | 3.2 | 3.1 |
| N1 | | 0.4 | 0.4 | 0.7 | 0.7 | 0.5 | 0.3 | 0.4 | 0.7 | 0.5 |
| N2 | | 0.7 | 0.5 | 0.5 | 0.4 | nd | nd | 0.4 | 0.5 | 0.4 |
| N3 | | nd | nd | nd | nd | nd | nd | 0.9 | 0.5 | 0.6 |
| N4 | | nd | nd | nd | nd | nd | nd | 0.4 | 0.5 | 0.7 |
| N5 | | nd | nd | nd | nd | 0.5 | 0.7 | 0.4 | 0.5 | 0.5 |
| N6 | | nd | nd | nd | nd | nd | nd | 0.4 | 0.5 | 0.5 |
| N7 | | 0.4 | 0.4 | 0.6 | 0.7 | nd | nd | 1.0 | 0.5 | 0.7 |
| N8 | | 0.4 | 0.5 | 0.5 | 0.5 | nd | nd | 0.4 | 0.5 | 0.6 |
| N9 | | 0.4 | 0.6 | 0.7 | 0.5 | nd | nd | 0.4 | 0.5 | 0.4 |
| N10 | | nd | nd | nd | nd | nd | nd | 0.3 | 0.5 | 0.4 |
| N11 | | nd | nd | nd | nd | nd | nd | 0.4 | 0.5 | 0.5 |
| N12 | | nd | nd | nd | nd | nd | nd | 0.5 | 0.7 | 0.8 |
| N13 | | nd | nd | nd | nd | nd | nd | 0.4 | 0.7 | 0.3 |
| N14 | | 0.7 | 0.5 | 0.5 | 0.5 | 0.9 | 0.7 | 0.5 | 0.5 | 0.5 |
| N15 | | 0.4 | 0.6 | 0.4 | 1.0 | 0.5 | 0.8 | 0.4 | 0.5 | 0.4 |
| N16 | | 0.8 | 0.2 | 0.5 | 0.6 | 0.5 | 0.4 | 0.5 | 0.7 | 0.5 |
| N17 | | 0.8 | 0.5 | 0.9 | 0.4 | 0.6 | 0.7 | 0.4 | 0.5 | 0.6 |
| N18 | | 0.3 | 0.4 | 0.7 | 0.5 | 0.6 | 0.6 | 0.4 | 0.6 | 0.9 |
| N19 | | 0.4 | 0.5 | 0.5 | 0.8 | nd | nd | 0.5 | 0.8 | 0.8 |
| N20 | | 0.6 | 0.6 | 0.4 | 0.6 | 0.7 | 0.5 | 0.8 | 0.7 | 1.0 |
| N21 | | 0.7 | 0.7 | 0.6 | 0.5 | 0.5 | 0.4 | 0.4 | 0.7 | 0.6 |
| N22 | | 0.4 | 0.5 | 0.7 | 0.5 | 0.5 | 0.7 | 0.4 | 0.6 | 0.3 |
| N23 | | 0.5 | 0.5 | 0.7 | 0.5 | nd | nd | 0.4 | 0.6 | 0.5 |
| N24 | | nd | nd | nd | nd | 0.5 | 0.5 | 0.5 | 0.7 | 0.7 |
| N25 | | nd | nd | nd | nd | 0.8 | 0.5 | 0.8 | 0.6 | 0.5 |
| N26 | | nd | nd | nd | nd | 0.5 | 0.6 | 0.4 | 0.6 | 0.4 |
| N27 | | nd | nd | nd | nd | 0.4 | 0.6 | 0.8 | 1.0 | 0.4 |

The following Table 4 summarizes the results of the ELISA assays based on recombinant proteins, employing serum samples from *T. gondii* seropositive and seronegative humans. In each column are reported the number and the corresponding percentages of reactive sera. From Table 4 it clearly results that the sensitivity of the assay (see the $2^{nd}$ column reporting the occurrence of false negatives) is improved when using the chimeric antigens of the invention. This improvement is evident with respect to both the use of single antigenic fragments and the use of a collection or mixtures (Mix-Tx-1.16/Tx-4.18/Tx-2.a, Mix-Tx-1.16/Tx-4.18/Tx-2.a, Mix-Tx-1.16/Tx-2.a/Tx-11.b) of the single different antigenic fragments.

TABLE 4

| GST-fusion protein | Sera from *T. gondii* infected subjects | Sera from *T. gondii* uninfected subjects |
|---|---|---|
| Tx-15.11 | 28/34 (82.4%) | 0/15 |
| Tx-1.11 | 29/33 (87.9%) | 0/15 |
| Tx-1.16 | 31/34 (91.2%) | 0/15 |
| Tx-4.18 | 27/33 (81.8%) | 0/15 |

TABLE 4-continued

| GST-fusion protein | Sera from T. gondii infected subjects | Sera from T. gondii uninfected subjects |
| --- | --- | --- |
| Tx-2.a | 21/23 (91.3%) | 0/14 |
| Tx-11.b | 18/23 (78.3%) | 0/14 |
| Mix-Tx-1.16/Tx-4.18/Tx-2.a | 35/36 (97.2) | 0/27 |
| Chimera EC2 | 36/36 (100%) | 0/27 |
| Mix-Tx-15.11/Tx-1.11/Tx-11.b | 35/36 (97.2%) | 0/27 |
| Chimera EC3 | 36/36 (100%) | 0/27 |
| Mix-Tx-1.16/Tx-2.a/Tx-11.b | 34/36 (94.4%) | 0/27 |
| Chimera EC4 | 36/36 (100%) | 0/27 |

Immunoreactivity of Single Antigenic Domains Within the Chimeric Recombinant Antigens with IgG Antibodies of Sera from T. gondii Infected Individuals To verify that the chimeric antigens retain the immunoreactivity of the single antigen fragments used for their construction, human sera that specifically reacted, in ELISA assays, with single antigen fragments, were adsorbed with different combinations of single antigens and then assayed with the chimeric proteins. To this aim, distinct combinations of the antigen fragments, expressed as GST-fusion products, were coated onto Maxisorb-multiwells plates (Nunc) at a concentration of 10 μg/ml in coating buffer (50 mM NaHCO$_3$, pH 9.6) and then incubated overnight at 4° C. The plates were extensively washed and subsequently incubated for 30 min. at 37° C. with serum samples (20 μl/well) in blocking solution (5% non-fat dry milk, 0.05% Tween-20 in PBS). The fragment-specific antibody-depleted sera were recovered from each well, added to a new well, incubated for 30 min., and the same procedure was repeated 6 more times. Samples that have been depleted for specific antibodies against a single or multiple antigen fragments were finally analyzed by ELISA assays on the chimeric antigens. For this purpose, the chimeric antigens EC2, EC3 and EC4, as GST-fusion products, were coated overnight at 4° C. onto Maxisorb-multiwells plates at a concentration of 5 μg/ml. The coated plates were blocked and subsequently incubated for 1 h at 37° C. with the antibody-depleted human sera diluted 1:100 in blocking solution. Plates were extensively washed and anti-human-IgG alkaline phosphatase-conjugated antibodies (Sigma-Aldrich, USA), diluted 1:7500 in blocking solution, was then added to each well. Finally, the chromogenic substrate p-nitrophenyl phosphate (Sigma-Aldrich, USA) revealed the enzymatic activity. The results were recorded as the difference between the absorbance at 405 and 620 nm, detected by an automated ELISA reader (Labsystem Multiskan, Finland). For each sample the assay was done in duplicate and average values were calculated.

Biochemical Modification of EC2 and EC3 Chimeric Antigens

To analyze the immunoreactivity of the chimeric antigens EC2 and EC3 with specific anti-Toxoplasma IgM antibodies in patient sera, the recombinant proteins were chemically modified by biotinilation. To this aim, the purified GST-EC2 and GST-EC3, diluted at a concentration of 1 mg/ml in PBS were incubated in the presence of a five-fold molar excess of sulfosuccinimidyl-6-(biotin-amido)hexanoate (Sulfo-NHS-LC-Biotin from Pierce, USA) for 3 hours on ice. The proteins were then dialyzed overnight against PBS to remove excess of non-reacted and hydrolyzed biotin reagents. Levels of biotin incorporation into chimeric antigens was determined by using "EZ Biotin Quantitation Kit" (Pierce, USA), resulting in 1.4 biotin/molecule for GST-EC2 and 1.3 biotin/molecule for GST-EC3. The biotin-labeled products were finally diluted at a concentration of 0.5 mg/ml and stored at −20° C. until use.

Immunoreactivity of the Biotin-Labeled EC2 and EC3 with Toxoplasma-Specific IgM Antibodies: IgM Rec-ELISA To investigate the immunoreactivity of recombinant antigens with Toxoplasma-specific immunoglobulins M, a double-sandwich immunoassay was employed (IgM Rec-ELISA). Maxisorb plates (Nunc, USA) were coated with anti-human IgM antibodies (Sigma-Aldrich, USA) at a concentration of 10 μg/ml in coating buffer (50 mM NaHCO$_3$, pH 9.6). Plates were blocked with 3% bovine serum albumin in PBS (blocking solution) for 1 h at 37° C. and subsequently incubated for 1 h at 37° C. with serum samples in blocking solution. Plates were washed and then incubated for 2 h at room temperature with the biotin-labeled GST-fusion proteins, diluted in blocking solution. After being extensively washed the plates were incubated for 1 h at room temperature with horseradish peroxidase-conjugated streptavidin (Pierce, USA) at a concentration of 1 μg/ml in blocking solution. Finally, the enzymatic activity was revealed incubating plates for 30 min. at room temperature with the substrate tetramethylbenzidine (Sigma-Aldrich, USA). Results were recorded as the difference between the absorbance at 450 and 620 nm, detected by an automated ELISA reader (Labsystem Multiskan, Finland). For each sample the assay was done in duplicate and average values were calculated.

Thermal Stability of the Biotin-Labeled Chimeric Antigens

In order to determine the thermal stability of the biotin-labeled GST-EC2 and GST-EC3, recombinant products were diluted at a concentration of 5 μg/ml in the commercial buffer "Stabilzyme" (SurModics, USA) and stored at +4° C. until use. After different interval times (up to 80 days), the immunoreactivity of recombinant proteins in the IgM Rec-ELISA analysis was assessed and results obtained analyzing the corresponding products maintained frozen at −20° C. were compared. The IgM Rec-ELISA was performed as described above, using the biotin-labeled GST-EC2 and GST-EC3 antigens at a final concentration of 500 ng/ml in blocking solution (3% BSA in PBS) and human sera diluted 1:100 in blocking solution. For each sample the assay was done in duplicate and average values were calculated. The ID50, calculated as day-limit when the 50% of toxoplasma-specific IgM-immunoreactivity was measured, were 189 days and 97 days for GST-EC2 and GST-EC3, respectively. These findings clearly indicate that the chimeric antigens of the invention are stable in diluted solutions for a long time, which a fundamental requisite for the commercial usefulness of a recombinant product.

Expanded Evaluation of IgM Rec-ELISA

The biotin-labeled GST-EC2 and GST-EC3 chimeric antigens Were assayed with IgM antibodies in sera from T. gondii infected individuals and the results of the IgM Rec-ELISAs were compared with those obtained with commercial assays employing lysed, whole-cell Toxoplasma antigen (VIDAS system from bioMerieux, France; ETI-TOXOK-M Reverse-PLUS from DiaSorin, Italy). To this aim, serum samples from women who acquired primary toxoplasmosis during gestation and referred for post-natal follow-up at the Center for Perinatal Infection of Campania Region, Italy, were assayed. The bioMerieux VIDAS Toxo IgG and IgM assays were used to select three groups of serum samples for the Toxoplasma IgM Rec-ELISA performance evaluation. Group A (n=22) was composed of samples negative for T. gondii-specific IgM and IgG antibody as measured by the VIDAS Toxo IgM and IgG assays. Group B (n=18) was composed of samples with a serological profile consistent with a chronic infection (presence of *T. gondii*-specific IgG antibody and absence of *T. gondii*-specific IgM as measured by the VIDAS Toxo IgM and IgG assays, respectively). Group C (n=50) was composed of samples with a serological profile consistent with an acute infection (presence of *T. gondii*-specific IgM and IgG antibodies as measured by the VIDAS Toxo IgM and IgG assays). IgM Rec ELISA was performed as described above and for each serum sample the assay was done in duplicate and average values were calculated.

The following Table 5 shows the IgM reactivity of the biotin-labeled GST-EC2 and GST-EC3 chimeric antigens, compared to the results obtained with commercial assays (VIDAS and ETI-TOXO-K), by using sera from group A (A1-A22), group B (B1-B18) and group C(C1-C50). The *Toxoplasma*-specific IgG levels, calculated as International Units (IU) are also reported. For each biotin-labeled GST-fusion product the cut-off was determined as the mean plus two times the standard deviation of the absorbency readings obtained from the *T. gondii*-specific IgM negative sera (groups A and B, n=40). Cut-off values for VIDAS IgM, ETI-TOXOK-M Reverse-PLUS, GST-EC2 and GST-EC3 were 0.650, 0.500, 0.343 and 0.378, respectively. Values typed in bold indicate a positive response.

TABLE 5

| Serum | Toxo-IgG (UI/ml) | VIDAS IgM | ETI-TOXOK-M Reverse-PLUS | IgM Rec-ELISA GST-EC2 | IgM Rec-ELISA GST-EC3 |
|---|---|---|---|---|---|
| A1 | 0 | 0.05 | 0.397 | 0.268 | 0.256 |
| A2 | 4 | 0.22 | 0.317 | 0.263 | 0.270 |
| A3 | 0 | 0.18 | 0.252 | 0.264 | 0.237 |
| A4 | 0 | 0.05 | 0.375 | 0.324 | 0.241 |
| A5 | 2 | 0.17 | 0.272 | 0.298 | 0.222 |
| A6 | 0 | 0.03 | 0.288 | 0.270 | 0.234 |
| A7 | 0 | 0.19 | 0.210 | 0.215 | 0.379 |
| A8 | 0 | 0.10 | 0.108 | 0.203 | 0.296 |
| A9 | 0 | 0.06 | 0.324 | 0.314 | 0.291 |
| A10 | 0 | 0.09 | 0.339 | 0.325 | 0.286 |
| A11 | 0 | 0.05 | 0.193 | 0.223 | 0.271 |
| A12 | 2 | 0.08 | 0.134 | 0.268 | 0.378 |
| A13 | 4 | 0.12 | 0.115 | 0.309 | 0.335 |
| A14 | 0 | 0.23 | 0.115 | 0.221 | 0.286 |
| A15 | 0 | 0.06 | 0.230 | 0.281 | 0.374 |
| A16 | 2 | 0.08 | 0.132 | 0.317 | 0.269 |
| A17 | 1 | 0.18 | 0.123 | 0.277 | 0.281 |
| A18 | 0 | 0.35 | 0.097 | 0.316 | 0.279 |
| A19 | 0 | 0.28 | 0.346 | 0.274 | 0.272 |
| A20 | 0 | 0.09 | 0.054 | 0.259 | 0.132 |
| A21 | 0 | 0.61 | 0.206 | 0.24 | 0.312 |
| A22 | 0 | 0.06 | 0.127 | 0.238 | 0.233 |
| B1 | 24 | 0.06 | 0.239 | 0.255 | 0.189 |
| B2 | 10 | 0.09 | 0.076 | 0.283 | 0.304 |
| B3 | 44 | 0.14 | 0.124 | 0.265 | 0.261 |
| B4 | 44 | 0.28 | 0.195 | 0.298 | 0.216 |
| B5 | 25 | 0.1 | 0.131 | 0.273 | 0.185 |
| B6 | 57 | 0.12 | 0.164 | 0.296 | 0.293 |
| B7 | 12 | 0.22 | 0.185 | 0.257 | 0.194 |
| B8 | 58 | 0.12 | 0.148 | 0.255 | 0.248 |
| B9 | 56 | 0.4 | 0.174 | 0.232 | 0.268 |
| B10 | 19 | 0.09 | 0.068 | 0.290 | 0.194 |
| B11 | 56 | 0.16 | 0.136 | 0.179 | 0.221 |
| B12 | 45 | 0.12 | 0.139 | 0.235 | 0.181 |
| B13 | 87 | 0.12 | 0.096 | 0.207 | 0.218 |
| B14 | 27 | 0.15 | 0.144 | 0.196 | 0.174 |
| B15 | 33 | 0.46 | 0.242 | 0.285 | 0.378 |
| B16 | 13 | 0.04 | 0.064 | 0.161 | 0.177 |
| B17 | 67 | 0.13 | 0.111 | 0.177 | 0.213 |
| B18 | 53 | 0.27 | 0.170 | 0.238 | 0.165 |
| C1 | 28 | 5.37 | 1.04 | 0.350 | 0.548 |
| C2 | 255 | 3.86 | 1.49 | 0.546 | 0.498 |
| C3 | 78 | 3.01 | 1.38 | 0.471 | 0.867 |
| C4 | 1358 | 2.28 | 1.17 | 0.464 | 0.453 |
| C5 | 178 | 2.31 | 1.27 | 0.598 | 0.406 |
| C6 | 155 | 2.00 | 0.97 | 0.993 | 0.720 |
| C7 | 109 | 3.20 | 1.76 | 0.794 | 0.642 |
| C8 | 99 | 3.16 | 1.78 | 0.572 | 0.389 |
| C9 | 103 | 2.28 | 1.34 | 1.056 | 1.222 |
| C10 | 85 | 2.22 | 1.44 | 0.930 | 0.704 |
| C11 | 70 | 1.01 | 0.79 | 0.416 | 0.376 |
| C12 | 26 | 1.34 | 0.93 | 0.392 | 0.461 |
| C13 | 36 | 1.22 | 0.86 | 0.532 | 0.499 |
| C14 | 156 | 0.99 | 0.58 | 0.534 | 0.833 |
| C15 | 204 | 0.93 | 0.90 | 0.810 | 0.710 |
| C16 | 133 | 1.13 | 0.85 | 0.465 | 0.322 |
| C17 | 183 | 1.14 | 0.82 | 0.320 | 0.327 |
| C18 | 242 | 0.90 | 0.71 | 0.497 | 0.500 |
| C19 | 80 | 1.00 | 0.79 | 0.444 | 0.706 |
| C20 | 258 | 1.40 | 0.88 | 2.678 | 0.484 |
| C21 | 278 | 1.69 | 1.06 | 0.703 | 0.509 |
| C22 | 246 | 1.25 | 0.76 | 1.094 | 0.780 |
| C23 | 59 | 1.23 | 0.71 | 0.495 | 1.499 |
| C24 | 38 | 0.78 | 0.87 | 0.584 | 0.455 |
| C25 | 130 | 0.76 | 0.92 | 0.562 | 0.545 |
| C26 | 262 | 0.84 | 0.65 | 0.649 | 0.551 |
| C27 | 168 | 0.96 | 0.85 | 1.439 | 0.938 |
| C28 | 126 | 0.78 | 0.80 | 2.475 | 1.160 |
| C29 | 197 | 1.38 | 0.61 | 0.544 | 0.358 |
| C30 | 127 | 0.86 | 0.52 | 0.847 | 0.531 |
| C31 | 72 | 1.28 | 0.93 | 1.756 | 0.891 |
| C32 | 130 | 0.77 | 0.71 | 0.505 | 0.381 |
| C33 | 439 | 1.00 | 0.66 | 0.834 | 0.464 |
| C34 | 83 | 0.66 | 1.32 | 1.162 | 0.989 |
| C35 | 178 | 0.89 | 0.87 | 0.694 | 0.487 |
| C36 | 560 | 0.86 | 0.69 | 0.817 | 0.628 |
| C37 | 223 | 0.96 | 0.73 | 0.531 | 0.819 |
| C38 | 242 | 0.98 | 0.41 | 0.379 | 0.318 |
| C39 | 118 | 1.16 | 0.84 | 0.420 | 0.380 |
| C40 | 232 | 1.39 | 1.01 | 0.490 | 0.467 |
| C41 | 213 | 1.03 | 1.05 | 0.750 | 0.822 |
| C42 | 243 | 1.06 | 0.97 | 0.534 | 0.502 |
| C43 | 154 | 0.75 | 0.73 | 0.455 | 0.337 |
| C44 | 35 | 1.90 | 1.51 | 0.383 | 1.008 |
| C45 | 667 | 0.85 | 1.01 | 0.366 | 0.285 |
| C46 | 275 | 0.95 | 0.99 | 0.411 | 0.544 |
| C47 | 157 | 1.93 | 1.36 | 0.382 | 0.464 |
| C48 | 1037 | 1.08 | 0.51 | 0.385 | 0.301 |
| C49 | 92 | 1.31 | 0.68 | 0.537 | 0.427 |
| C50 | 255 | 0.69 | 0.69 | 0.354 | 0.801 |

The following Table 6 shows the performance characteristics of the commercial assays (VIDAS IgM and ETI-TOXOK-M Reverse PLUS), compared to the results obtained with the biotin-labeled EC2 and EC3 chimeric antigens (IgM Rec-ELISA). From Table 6 it clearly results that both specificity and positive predictive values of the assays (see the 3$^{rd}$ column reporting the occurrence of false positives) reached the maximum (100%) when using the chimeric antigens of the invention. With regard to sensitivity and agreement, both the commercial test ETI-TOXOK-M employing lysed, whole-cell *Toxoplasma* antigen and the IgM rec-ELISA with the chimeric antigen EC2 display identical performance characteristics, with both values very close to 100%.

TABLE 6

| Diagnostic test | Sensitivity (%) | Specificity (%) | Agreement (%) | PPV* (%) | NPV* (%) |
|---|---|---|---|---|---|
| VIDAS IgM | 100 | 100 | 100 | 100 | 100 |
| ETI-TOXOK-M | 98.0 | 100 | 98.9 | 100 | 97.6 |
| EC2-IgM Rec-ELISA | 98.0 | 100 | 98.9 | 100 | 97.6 |
| EC3-IgM Rec-ELISA | 84.0 | 100 | 91.1 | 100 | 83.3 |

*PPV, positive predictive value; NPV, negative predictive value.

Finally, the immunoreactivity of the biotin-labeled GST-EC2 and GST-EC3 antigens with IgM antibodies in sera from infants with congenital toxoplasmosis was investigated. In a retrospective study, sera from 30 infants of mothers with primary *T. gondii* infection during pregnancy were analyzed. Twenty infants had congenital toxoplasmosis and ten was uninfected, as demonstrated by the persistence or disappearance of *Toxoplasma*-specific IgG antibodies after 12 months of age, respectively. Within the infected patient cohort, the gestational age at the time of maternal infection was the second trimester in 6 mothers and the third trimester in 14 mothers. 30 serum samples from infected and uninfected infants were analyzed by IgM Rec-ELISA, and results obtained with commercial assays employing the whole-cell *Toxoplasma* antigen (ELFA-IgM and ETI-TOXOK-M Reverse PLUS) were compared. Specific levels of anti-*Toxoplasma* IgG ranged from 28 to 1147 IU/ml for sera from infected infants and from 19 to 170 IU/ml for sera from uninfected subjects. For every GST-fusion product the cut-off value was determined as the mean plus 2SD of the absorbency readings obtained with sera from uninfected infants. In Table 7 are summarized the results of the IgM Rec-ELISAs with individual sera from infected infants. Overall, the number of IgM-reactive sera ranged from 70% (14/20) to 50% (10/20) using the GST-EC2 and GST-EC3 antigens, respectively. In contrast, only 7 out of 20 infected infants (35%) had positive results when ELFA-IgM or ETI-TOXOK-M assays were employed. Among uninfected infants, none of the sera recognized GST-EC2 and GST-EC3 antigens in the IgM Rec-ELISA or resulted to be positive using commercial assays.

In conclusion, these results demonstrate that the use of recombinant chimeric antigens is effective in distinguishing *T. gondii*-infected from uninfected individuals, having comparable or even better assay performance with respect of using the whole-cell tachyzoite antigen, and could provide the basis for standardized commercial immunoassays for toxoplasmosis serodiagnosis.

TABLE 7

Toxoplasma-specific IgM reactivity of serum samples from 30 infants born to mothers with primary *T. gondii* infection acquired during pregnancy[a]

| Patient no. | Time after birth (wk) | Onset[b] | IgG levels (IU/ml) | ELFA-IgM cutoff[c] | ETI-ToxoM cutoff[c] | IgM Rec-ELISA cutoff[d] GST-EC2 | IgM Rec-ELISA cutoff[d] GST-EC3 |
|---|---|---|---|---|---|---|---|
| T1 | 1 | B | 169 | 6.41 | 2.66 | 2.479 | 0.542 |
| T2 | 2 | B | 988 | 0.73 | 0.15 | 0.360 | 0.270 |
| T3 | 2 | Sub | 300 | 0.09 | 0.13 | 0.212 | 0.209 |
| T4 | 3 | Sub | 57 | 0.05 | 0.23 | 0.206 | 0.211 |
| T5 | 3 | Sub | 124 | 0.13 | 1.62 | 0.641 | 1.103 |
| T6 | 4 | Sub | 218 | 0.04 | 0.09 | 0.452 | 0.269 |
| T7 | 4 | S | 157 | 2.61 | 1.62 | 1.522 | 0.225 |
| T8 | 4 | S | 172 | 3.98 | 1.50 | 1.804 | 0.353 |
| T9 | 5 | S | 1147 | 0.07 | 0.10 | 0.519 | 0.206 |
| T10 | 5 | B | 47 | 0.11 | 0.12 | 0.272 | 0.276 |
| T11 | 6 | Sub | 28 | 0.10 | 0.18 | 2.617 | 0.731 |
| T12 | 6 | Sub | 136 | 0.07 | 0.11 | 0.314 | 0.216 |
| T13 | 7 | S | 209 | 0.88 | 0.47 | 0.683 | 0.217 |
| T14 | 8 | Sub | 43 | 0.06 | 0.07 | 0.196 | 0.213 |
| T15 | 8 | B | 160 | 0.82 | 0.08 | 0.206 | 0.219 |
| T16 | 8 | B | 64 | 0.02 | 0.40 | 0.231 | 0.228 |
| T17 | 8 | Sub | 145 | 0.31 | 0.57 | 0.985 | 0.314 |
| T18 | 9 | Sub | 300 | 6.37 | 1.30 | 0.548 | 0.315 |
| T19 | 12 | Sub | 196 | 0.05 | 0.17 | 0.463 | 0.268 |
| T20 | 12 | Sub | 75 | 0.05 | 0.07 | 0.237 | 0.222 |
| N1 | 5 | | 90 | 0.38 | 0.06 | 0.237 | 0.218 |
| N2 | 5 | | 170 | 0.06 | 0.07 | 0.204 | 0.200 |
| N3 | 5 | | 66 | 0.23 | 0.09 | 0.238 | 0.235 |
| N4 | 3 | | 44 | 0.07 | 0.12 | 0.176 | 0.209 |
| N5 | 9 | | 41 | 0.05 | 0.05 | 0.209 | 0.193 |
| N6 | 5 | | 66 | 0.07 | 0.06 | 0.194 | 0.196 |
| N7 | 8 | | 13 | 0.09 | 0.06 | 0.193 | 0.201 |
| N8 | 9 | | 13 | 0.14 | 0.06 | 0.208 | 0.231 |
| N9 | 6 | | 19 | 0.28 | 0.07 | 0.184 | 0.215 |
| N10 | 5 | | 20 | 0.13 | 0.05 | 0.189 | 0.240 |

Notes to Table 7

[a] Serum samples from *T. gondii* infected (T1-T20) or uninfected children (N1-N10) were analyzed by IgM Rec-ELISAs with GST-EC2 and GST-EC3 antigens or by commercial assays (ELFA-IgM and ETI-TOXO-M).
[b] Severity of clinical onset: S. severe; B. benign; Sub. subclinical.
[c] Cutoff values for the ELFA-IgM and ETI-TOXO-M assays were 0.65 and 0.41 as indicated by manufacturers. respectively. Bold type, values > cutoff.
[d] Cutoff values for the IgM Rec-ELISA using GST-EC2 and GST-EC3 antigens were 0.25 and 0.26. respectively. Bold type, values > cutoff.

Construction of DNA Vectors Directing the Expression of Fusion Products in the Cytoplasm of Mammalian Cells The DNA encoding for the chimeric antigens EC2 and EC3 were amplified by PCR from bacterial vectors pGEX-EC2 and pGEX-EC3. Specific primers to introduce the Hind-III restriction site followed by a translation start-codon and a stop-codon followed by the Xba-1 site, at their 5'- and 3'-DNA ends, respectively, were used: EC2-for, 5'-GGCCAAGCT-TGAAATGGGTACTAGTCGGCTCCC-3' (SEQ ID NO: 43); EC2-rev, 5'-CCGGTCTAGAGAGCCGATTTTGCT-GACCCTGC-3' (SEQ ID NO:44); EC3-for, 5'-GGC-CAAGCTTGAAATGGTGGCTGCCTTGGGAGGCCTT-3' (SEQ ID NO: 45); EC3-rev, 5'-CCGGTCTAGAGCTAAC-CAGAAGATTCAGACTCAG-3' (SEQ ID NO: 46).

To direct the expression of the foreign proteins in the cytoplasm of mammalian cells the amplified DNA fragments were cloned in the Hind-III and Xba-1 sites of the mammalian vector pcDNA3.1 (Invitrogen, USA), under the transcriptional control of the cytomegalovirus early promoter, to give pcDNA-EC2 and pcDNA-EC3 vectors, respectively. The plasmids were purified from transformed *E. coli* by using "EndoFree plasmid kit" (Qiagen, Germany), dissolved in endotoxin-free PBS and stored at −20° C.

DNA Immunization and *T. gondii* Challenge

Seven- to eight-week-old BALB/c mice were used for this study. Mice (10 per group) received injections of 50 μl of DNA as follows: 1) pcDNA-EC2; 2) pcDNA-EC3; 3) pcDNA-EC2 and pcDNA-EC3 plasmid mixture; 4) empty pcDNA3.1. DNA was given to mice into each anterior tibial muscle (final plasmid concentration, 2 mg/ml). Three and six weeks after vaccination the injections were repeated using the same protocol. Tail bleeds were performed on vaccinated mice 3 weeks after the last DNA injection to ascertain the presence of specific anti-EC2 and anti-EC3 antibodies. At the same time spleens from two mice in each group were isolated and used in ELISPOT analysis while the remaining mice were challenged orally with *T. gondii*, Pruigneau isolate, cysts (30 parasite cysts per mouse). Six weeks after the oral challenge, immunized mice were killed and their brains were removed. Cysts were obtained by homogenizing the brains of infected mice. The mean number of cysts and bradyzoites per brain was determined microscopically by counting 4 samples (10 µl each) of each homogenate and by quantitative PCR1 respectively. The results are illustrated in FIGS. 5A and 5B.

Microscopic examination showed 84% and 94% reduction in brain cyst burden when BALB/c mice were immunized with pcDNA-EC2 and pcDNA-EC3, respectively, compared with control pcDNA3.1 empty plasmid vaccinated mice ($p<0.05$). The protective effect was apparently abolished when mice were vaccinated with pcDNA-EC2 combined with pcDNA-EC3 (FIG. 5A). Quantitative PCR however displayed a reduction in bradyzoite burden by 93% and 98% when the mice were respectively immunized with pcDNA-EC2 or pcDNA-EC3, compared with control pcDNA3.1 empty plasmid vaccinated mice ($p<0.05$). Also, with PCR analysis a reduction of parasite burden by 97.5% was observed when the mice were immunized with a combination of pcDNA-EC2 and pcDNA-EC3 (FIG. 5B). The discrepancy between the outcome obtained by microscopy and quantitative PCR reflect a variation in the number of parasites (bradyzoites) per cyst.

Analysis of the Antibody Response of Immunized Mice

Serum samples from immunized mice were tested, in ELISA assays, by coating Maxisorb-plates (Nunc, Denmark) with GST fusion proteins at a concentration of 5 µg/ml in 50 mM $NaHCO_3$, pH 9.6. After incubation overnight at 4° C., plates were left 1 hour at 37° C. in blocking solution (5% non-fat dry milk, 0.05% Tween-20 in PBS) and subsequently incubated for 1 h at 37° C. with mice sera diluted 1:100 in blocking solution. Plates were then washed and anti-mouse-IgG, or anti-mouse-IgG1, or anti-mouse-IgG2a HRP-conjugated antibodies (Sigma-Aldrich, USA) were added to each well. Tetramethylbenzidine (Sigma-Aldrich, USA) was used to reveal enzymatic activity. The results were recorded as the difference between the absorbance at 450 nm and 620 nm, detected by an automated ELISA reader (Labsystem Multiskan, Finland). For each serum sample the assay was done in duplicate and average values were calculated. The results illustrated in FIGS. 6A and 6B demonstrated a production of IgG antibodies against the chimeric antigen EC3 in 25% of the mice immunized with pcDNA-EC3 and 28% of the mice immunized with the mixture of pcDNA-EC2 and pcDNA-EC3 (FIGS. 6A and 6B). As shown in the following Table 8, IgG antibodies were of subclass IgG1 as well as IgG2a, indicating a shift towards a more Th1-like immune response after DNA immunization.

TABLE 8

Production of anti-EC3 IgG subclasses[a]

| Mouse No. | IgG1 (OD) | IgG2a (OD) |
|---|---|---|
| EC3.1 | 0.080 | 0.581 |
| EC3.2 | 0.179 | 0.075 |
| EC2 + EC3.1 | 0.168 | 0.072 |
| EC2 + EC3.2 | 1.125 | 0.480 |

[a]Sera from immunized mice were analyzed in ELISA against GST-EC3 using anti-mouse-IgG1 or anti-mouse-IgG2a antibodies. Cutoff values: 0.119 (IgG1) and 0.158 (IgG2a).
OD, Optical Density;
Bold type, OD > cutoff.

By analysis of single antigenic fragments Applicants found that the strongest antibody response was raised against the GRA3 antigen. Production of detectable levels of IgG antibodies was not demonstrated towards the chimeric antigen EC2. To detect IFN-gamma production, through MHC II stimulation, recombinant antigens were used for in vitro stimulation of spleen cells from immunized mice in an ELISPOT assay. A specific $CD4^+$ T cell response was not detected, thus indicating that the DNA vaccines generated an immune response mainly characterized by specific $CD8^+$ memory T cells.

Statistical Analysis

In the experiments described above the levels of significance for the differences between the groups of mice were determined by use of Student's t test (2-tailed); equal variance in the groups was assumed.

In conclusion, brain cyst burden was strongly reduced in mice who received either pcDNA-EC2 or pcDNA-EC3 prior to oral challenge with parasite cysts. Moreover, a prominent reduction in the total bradyzoite load was demonstrated, in mice vaccinated with the mixture of pcDNA-EC2 and pcDNA-EC3. This observation indicates that, when given in combination, the chimeric antigens might have an inhibitory effect on cyst development by strongly reducing their size. No evidence of correlation was found between induction of antibody production and protection against oral challenge. Thus, the observed resistance in groups of mice immunized with EC2 and EC3 towards infection seems to results from a cell-mediated immune response, most probably involving the generation of CD8+ memory T cells specific for the chimeric antigens.

The paper copy of the sequence listing submitted herewith and the corresponding computer readable form are both incorporated herein by reference in their entireties.

The invention claimed is:

1. A method for treatment of a disease or condition associated with presence of *Toxoplasma gondii* in an individual, the method comprising:
  administering to the individual a therapeutically effective amount of a chimeric recombinant antigen to a subject in need thereof,
  wherein the chimeric recombinant antigen contains a chimeric fusion of at least three different antigenic fragments of *Toxoplasma gondii* polypeptides,
  wherein said antigenic fragments are B-cell epitopes which bind to *Toxoplasma gondii*-specific antibodies and
  wherein the at least three different antigenic fragments have an amino acid sequence selected from the group consisting of: SEQ ID NO: 2, SEQ ID NO: 4, SEQ ID NO: 6, SEQ ID NO: 8, SEQ ID NO: 10, and SEQ ID NO: 12.

2. The method of claim 1, wherein the *Toxoplasma gondii*-specific antibodies are extracted from sera of subjects who have been infected by *Toxoplasma gondii*.

3. The method of claim 1, wherein the at least three different antigenic fragments are linked by a covalent bond or by a peptide linker.

4. The method of claim 1, wherein the chimeric recombinant antigen is a recombinant antigen having the amino acid sequence SEQ ID NO: 28, SEQ ID NO: 30 or SEQ ID NO:32.

5. The method of claim 1, wherein the chimeric recombinant antigen is comprised in a vaccine.

6. A pharmaceutical composition, containing at least one chimeric recombinant antigen,
  wherein the chimeric recombinant antigen contains a chimeric fusion of at least three different antigenic fragments of *Toxoplasma gondii* polypeptides, and
  wherein said antigenic fragments are B-cell epitopes which bind to *Toxoplasma gondii*-specific antibodies and
  wherein the at least three different antigenic fragments have an amino acid sequence selected from the group consisting of: SEQ ID NO: 2, SEQ ID NO: 4, SEQ ID NO: 6, SEQ ID NO: 8, SEQ ID NO: 10, SEQ ID NO: 12.

7. The pharmaceutical composition of claim 6, wherein the *Toxoplasma gondii*-specific antibodies are extracted from sera of subjects who have been infected by *Toxoplasma gondii*.

8. The pharmaceutical composition of claim 6, wherein the three different antigenic fragments are linked by a covalent bond or by a peptide linker.

9. The pharmaceutical composition of claim 6, wherein the at least one recombinant antigen is a recombinant antigen having the amino acid sequence SEQ ID NO: 28, SEQ ID NO: 30 or SEQ ID NO:32.

10. The pharmaceutical composition according to claim 6, wherein the pharmaceutical composition is suitable for human and/or veterinary use.

11. The pharmaceutical composition according to claim 6, wherein the pharmaceutical composition is a vaccine.

12. A method of using a chimeric recombinant antigen, the method comprising:
  providing said chimeric recombinant antigen in a medicament for a subject in need thereof,
  wherein said recombinant antigen contains the chimeric fusion of at least three different antigenic fragments of *Toxoplasma gondii* polypeptides, wherein the three different antigenic fragments are B-cell epitopes, which bind to *Toxoplasma gondii*-specific antibodies and wherein the three different antigenic fragments have an amino acid sequence selected from the group consisting of: SEQ ID NO: 2, SEQ ID NO: 4, SEQ ID NO: 6, SEQ ID NO: 8, SEQ ID NO: 10, and SEQ ID NO: 12.

13. The method of claim 12, wherein the chimeric recombinant antigen is a chimeric recombinant antigen having the amino acid sequence SEQ ID NO:28, SEQ ID NO: 30 or SEQ ID NO:32.

14. A method for treating a *Toxoplasma gondii* infection in an individual, the method comprising:

administering to the individual a therapeutically effective amount of a chimeric antigen containing at least three different antigenic fragments having an amino acid sequence selected from the group consisting of: SEQ ID NO: 2, SEQ ID NO: 4, SEQ ID NO: 6, SEQ ID NO: 8, SEQ ID NO: 10, and SEQ ID NO: 12.

15. The method of claim 14, wherein the at least three different antigenic fragments are linked by a covalent bond or by a peptide linker.

16. The method of claim 15, wherein the peptide linker has SEQ ID NO:47.

17. The method of claim 14, wherein the chimeric antigen has amino acid sequence SEQ ID NO: 28, SEQ ID NO: 30 or SEQ ID NO:32.

18. A pharmaceutical composition containing at least one chimeric antigen, the at least one chimeric antigen containing at least three different antigenic fragments having an amino acid sequence selected from the group consisting of: SEQ ID NO: 2, SEQ ID NO: 4, SEQ ID NO: 6, SEQ ID NO: 8, SEQ ID NO: 10, and SEQ ID NO: 12.

19. The pharmaceutical composition of claim 18, wherein the three different antigenic fragments are linked by a covalent bond or by a peptide linker.

20. The method of claim 18, wherein the peptide linker has SEQ ID NO:47.

21. The pharmaceutical composition of claim 18, wherein the chimeric antigen has amino acid sequence SEQ ID NO: 28, SEQ ID NO: 30 or SEQ ID NO:32.

* * * * *

SEQUENCE LISTING

```
<160> NUMBER OF SEQ ID NOS: 47

<210> SEQ ID NO 1
<211> LENGTH: 297
<212> TYPE: DNA
<213> ORGANISM: Toxoplasma gondii
<220> FEATURE:
```

```
<221> NAME/KEY: CDS
<222> LOCATION: (1)..(297)

<400> SEQUENCE: 1 gct gcc ttg gga ggc ctt gcg gcg gat cag cct gaa aat cat cag gct      48
Ala Ala Leu Gly Gly Leu Ala Ala Asp Gln Pro Glu Asn His Gln Ala
1               5                   10                  15 ctt gca gaa cca gtt acg ggt gtg ggg gaa gca gga gtg tcc ccc gtc      96
Leu Ala Glu Pro Val Thr Gly Val Gly Glu Ala Gly Val Ser Pro Val
                20                  25                  30 aac gaa gct ggt gag tca tac agt tct gca act tcg ggt gtc caa gaa     144
Asn Glu Ala Gly Glu Ser Tyr Ser Ser Ala Thr Ser Gly Val Gln Glu
            35                  40                  45 gct acc gcc cca ggt gca gtg ctc ctg gac gca atc gat gcc gag tcg     192
Ala Thr Ala Pro Gly Ala Val Leu Leu Asp Ala Ile Asp Ala Glu Ser
        50                  55                  60 gat aag gtg gac aat cag gcg gag gga ggt gag cgt atg aag aag gtc     240
Asp Lys Val Asp Asn Gln Ala Glu Gly Gly Glu Arg Met Lys Lys Val
65                  70                  75                  80 gaa gag gag ttg tcg tta ttg agg cgg gaa tta tat gat cgc aca gat     288
Glu Glu Glu Leu Ser Leu Leu Arg Arg Glu Leu Tyr Asp Arg Thr Asp
                85                  90                  95 cgc cct ggt                                                         297
Arg Pro Gly <210> SEQ ID NO 2
<211> LENGTH: 99
<212> TYPE: PRT
<213> ORGANISM: Toxoplasma gondii

<400> SEQUENCE: 2

Ala Ala Leu Gly Gly Leu Ala Ala Asp Gln Pro Glu Asn His Gln Ala
1               5                   10                  15

Leu Ala Glu Pro Val Thr Gly Val Gly Glu Ala Gly Val Ser Pro Val
                20                  25                  30

Asn Glu Ala Gly Glu Ser Tyr Ser Ser Ala Thr Ser Gly Val Gln Glu
            35                  40                  45

Ala Thr Ala Pro Gly Ala Val Leu Leu Asp Ala Ile Asp Ala Glu Ser
        50                  55                  60

Asp Lys Val Asp Asn Gln Ala Glu Gly Gly Glu Arg Met Lys Lys Val
65                  70                  75                  80

Glu Glu Glu Leu Ser Leu Leu Arg Arg Glu Leu Tyr Asp Arg Thr Asp
                85                  90                  95

Arg Pro Gly

<210> SEQ ID NO 3
<211> LENGTH: 231
<212> TYPE: DNA
<213> ORGANISM: Toxoplasma gondii
<220> FEATURE:
<221> NAME/KEY: CDS
<222> LOCATION: (1)..(231)

<400> SEQUENCE: 3 gct acc gcg gcc acc gcg tca gat gac gaa ctg atg agt cga atc cga      48
Ala Thr Ala Ala Thr Ala Ser Asp Asp Glu Leu Met Ser Arg Ile Arg
1               5                   10                  15 aat tct gac ttt ttc gat ggt caa gca ccc gtt gac agt ctc aga ccg      96
Asn Ser Asp Phe Phe Asp Gly Gln Ala Pro Val Asp Ser Leu Arg Pro
                20                  25                  30
```

```
acg aac gcc ggt gtc gac tcg aaa ggg acc gac gat cac ctc acc acc    144
Thr Asn Ala Gly Val Asp Ser Lys Gly Thr Asp Asp His Leu Thr Thr
        35                  40                  45 agc atg gat aag gca tct gta gag agt cag ctt ccg aga aga gag cca    192
Ser Met Asp Lys Ala Ser Val Glu Ser Gln Leu Pro Arg Arg Glu Pro
 50                  55                  60 ttg gag acg gag cca gat gaa caa gaa gaa gtt cat ttc                231
Leu Glu Thr Glu Pro Asp Glu Gln Glu Glu Val His Phe
65                  70                  75

<210> SEQ ID NO 4
<211> LENGTH: 77
<212> TYPE: PRT
<213> ORGANISM: Toxoplasma gondii

<400> SEQUENCE: 4

Ala Thr Ala Ala Thr Ala Ser Asp Asp Glu Leu Met Ser Arg Ile Arg
1               5                   10                  15

Asn Ser Asp Phe Phe Asp Gly Gln Ala Pro Val Asp Ser Leu Arg Pro
            20                  25                  30

Thr Asn Ala Gly Val Asp Ser Lys Gly Thr Asp Asp His Leu Thr Thr
        35                  40                  45

Ser Met Asp Lys Ala Ser Val Glu Ser Gln Leu Pro Arg Arg Glu Pro
 50                  55                  60

Leu Glu Thr Glu Pro Asp Glu Gln Glu Glu Val His Phe
65                  70                  75

<210> SEQ ID NO 5
<211> LENGTH: 219
<212> TYPE: DNA
<213> ORGANISM: Toxoplasma gondii
<220> FEATURE:
<221> NAME/KEY: CDS
<222> LOCATION: (1)..(219)

<400> SEQUENCE: 5 agg agg act gga tgt cat gcc ttc agg gag aac tgc agc cct ggt aga     48
Arg Arg Thr Gly Cys His Ala Phe Arg Glu Asn Cys Ser Pro Gly Arg
1               5                   10                  15 tgt att gat gac gcc tcg cat gag aat ggc tac acc tgc gag tgc ccc     96
Cys Ile Asp Asp Ala Ser His Glu Asn Gly Tyr Thr Cys Glu Cys Pro
            20                  25                  30 aca ggg tac tca cgt gag gtg act tcc aag gcg gag gag tcg tgt gtg    144
Thr Gly Tyr Ser Arg Glu Val Thr Ser Lys Ala Glu Glu Ser Cys Val
        35                  40                  45 gaa gga gtc gaa gtc acg ctg gct gag aaa tgc gag aag gaa ttc ggc    192
Glu Gly Val Glu Val Thr Leu Ala Glu Lys Cys Glu Lys Glu Phe Gly
 50                  55                  60 atc agc gcg tca tcc tgc aaa tgc gat                                219
Ile Ser Ala Ser Ser Cys Lys Cys Asp
65                  70

<210> SEQ ID NO 6
<211> LENGTH: 73
<212> TYPE: PRT
<213> ORGANISM: Toxoplasma gondii

<400> SEQUENCE: 6

Arg Arg Thr Gly Cys His Ala Phe Arg Glu Asn Cys Ser Pro Gly Arg
1               5                   10                  15

Cys Ile Asp Asp Ala Ser His Glu Asn Gly Tyr Thr Cys Glu Cys Pro
            20                  25                  30
```

```
Thr Gly Tyr Ser Arg Glu Val Thr Ser Lys Ala Glu Glu Ser Cys Val
        35                  40                  45

Glu Gly Val Glu Val Thr Leu Ala Glu Lys Cys Glu Lys Glu Phe Gly
 50                  55                  60

Ile Ser Ala Ser Ser Cys Lys Cys Asp
 65                  70

<210> SEQ ID NO 7
<211> LENGTH: 393
<212> TYPE: DNA
<213> ORGANISM: Toxoplasma gondii
<220> FEATURE:
<221> NAME/KEY: CDS
<222> LOCATION: (1)..(393)

<400> SEQUENCE: 7 cca tcg gtc gtc aat aat gtc gca agg tgc tcc tac ggt gca gac agc      48
Pro Ser Val Val Asn Asn Val Ala Arg Cys Ser Tyr Gly Ala Asp Ser
 1               5                  10                  15 act ctt ggt cct gtc aag ttg tct gcg gaa gga ccc act aca atg acc      96
Thr Leu Gly Pro Val Lys Leu Ser Ala Glu Gly Pro Thr Thr Met Thr
             20                  25                  30 ctc gtg tgc ggg aaa gat gga gtc aaa gtt cct caa gac aac aat cag     144
Leu Val Cys Gly Lys Asp Gly Val Lys Val Pro Gln Asp Asn Asn Gln
         35                  40                  45 tac tgt tcc ggg acg acg ctg act ggt tgc aac gag aaa tcg ttc aaa     192
Tyr Cys Ser Gly Thr Thr Leu Thr Gly Cys Asn Glu Lys Ser Phe Lys
     50                  55                  60 gat att ttg cca aaa tta act gag aac ccg tgg cag ggt aac gct tcg     240
Asp Ile Leu Pro Lys Leu Thr Glu Asn Pro Trp Gln Gly Asn Ala Ser
 65                  70                  75                  80 agt gat aag ggt gcc acg cta acg atc aag aag gaa gca ttt cca gcc     288
Ser Asp Lys Gly Ala Thr Leu Thr Ile Lys Lys Glu Ala Phe Pro Ala
                 85                  90                  95 gag tca aaa agc gtc att att gga tgc aca ggg gga tcg cct gag aag     336
Glu Ser Lys Ser Val Ile Ile Gly Cys Thr Gly Gly Ser Pro Glu Lys
            100                 105                 110 cat cac tgt acc gtg aaa ctg gag ttt gcc ggg gct gca ggg tca gca     384
His His Cys Thr Val Lys Leu Glu Phe Ala Gly Ala Ala Gly Ser Ala
        115                 120                 125 aaa tcg gct                                                         393
Lys Ser Ala
    130

<210> SEQ ID NO 8
<211> LENGTH: 131
<212> TYPE: PRT
<213> ORGANISM: Toxoplasma gondii

<400> SEQUENCE: 8

Pro Ser Val Val Asn Asn Val Ala Arg Cys Ser Tyr Gly Ala Asp Ser
 1               5                  10                  15

Thr Leu Gly Pro Val Lys Leu Ser Ala Glu Gly Pro Thr Thr Met Thr
             20                  25                  30

Leu Val Cys Gly Lys Asp Gly Val Lys Val Pro Gln Asp Asn Asn Gln
         35                  40                  45

Tyr Cys Ser Gly Thr Thr Leu Thr Gly Cys Asn Glu Lys Ser Phe Lys
     50                  55                  60

Asp Ile Leu Pro Lys Leu Thr Glu Asn Pro Trp Gln Gly Asn Ala Ser
 65                  70                  75                  80
```

Ser Asp Lys Gly Ala Thr Leu Thr Ile Lys Lys Glu Ala Phe Pro Ala
                85                  90                  95

Glu Ser Lys Ser Val Ile Ile Gly Cys Thr Gly Gly Ser Pro Glu Lys
            100                 105                 110

His His Cys Thr Val Lys Leu Glu Phe Ala Gly Ala Ala Gly Ser Ala
        115                 120                 125

Lys Ser Ala
    130

<210> SEQ ID NO 9
<211> LENGTH: 237
<212> TYPE: DNA
<213> ORGANISM: Toxoplasma gondii
<220> FEATURE:
<221> NAME/KEY: CDS
<222> LOCATION: (1)..(237)

<400> SEQUENCE: 9

```
ccc cag gat gcc att tgc tcg gat tgg tcc gca tgg agc ccc tgc agt         48
Pro Gln Asp Ala Ile Cys Ser Asp Trp Ser Ala Trp Ser Pro Cys Ser
1               5                   10                  15 gta tcc tgc ggt gac gga agc caa atc agg acg cga act gag gtt tct         96
Val Ser Cys Gly Asp Gly Ser Gln Ile Arg Thr Arg Thr Glu Val Ser
            20                  25                  30 gct ccg caa cct gga aca cca aca tgt ccg gac tgc cct gcg ccc atg        144
Ala Pro Gln Pro Gly Thr Pro Thr Cys Pro Asp Cys Pro Ala Pro Met
        35                  40                  45 gga agg act tgc gtg gaa caa ggc gga ctt gaa gaa atc cgt gaa tgc        192
Gly Arg Thr Cys Val Glu Gln Gly Gly Leu Glu Glu Ile Arg Glu Cys
    50                  55                  60 agt gcg ggg gta tgt gct gtt gac gct gga tgt ggc gtc tgg gtt            237
Ser Ala Gly Val Cys Ala Val Asp Ala Gly Cys Gly Val Trp Val
65                  70                  75
```

<210> SEQ ID NO 10
<211> LENGTH: 79
<212> TYPE: PRT
<213> ORGANISM: Toxoplasma gondii

<400> SEQUENCE: 10

Pro Gln Asp Ala Ile Cys Ser Asp Trp Ser Ala Trp Ser Pro Cys Ser
1               5                   10                  15

Val Ser Cys Gly Asp Gly Ser Gln Ile Arg Thr Arg Thr Glu Val Ser
            20                  25                  30

Ala Pro Gln Pro Gly Thr Pro Thr Cys Pro Asp Cys Pro Ala Pro Met
        35                  40                  45

Gly Arg Thr Cys Val Glu Gln Gly Gly Leu Glu Glu Ile Arg Glu Cys
    50                  55                  60

Ser Ala Gly Val Cys Ala Val Asp Ala Gly Cys Gly Val Trp Val
65                  70                  75

<210> SEQ ID NO 11
<211> LENGTH: 678
<212> TYPE: DNA
<213> ORGANISM: Toxoplasma gondii
<220> FEATURE:
<221> NAME/KEY: CDS
<222> LOCATION: (1)..(678)

<400> SEQUENCE: 11 aac gaa ccg gtg gcc cta gct cag ctc agc aca ttc ctc gag ctc gtc         48

```
Asn Glu Pro Val Ala Leu Ala Gln Leu Ser Thr Phe Leu Glu Leu Val
1               5                   10                  15 gag gtg cca tgt aac tct gtt cat gtt cag ggg gtg atg acc ccg aat         96
Glu Val Pro Cys Asn Ser Val His Val Gln Gly Val Met Thr Pro Asn
            20                  25                  30 caa atg gtc aaa gtg act ggt gca gga tgg gat aat ggc gtt ctc gag        144
Gln Met Val Lys Val Thr Gly Ala Gly Trp Asp Asn Gly Val Leu Glu
        35                  40                  45 ttc tat gtc acg agg cca acg aag aca ggc ggg gac aca agc cga agc        192
Phe Tyr Val Thr Arg Pro Thr Lys Thr Gly Gly Asp Thr Ser Arg Ser
    50                  55                  60 cat ctt gcg tcg atc atg tgt tat tcc aag gac att gac ggc gtg ccg        240
His Leu Ala Ser Ile Met Cys Tyr Ser Lys Asp Ile Asp Gly Val Pro
65                  70                  75                  80 tca gac aaa gcg gga aag tgc ttt ctg aag aac ttt tct ggt gaa gac        288
Ser Asp Lys Ala Gly Lys Cys Phe Leu Lys Asn Phe Ser Gly Glu Asp
                85                  90                  95 tcg tcg gaa ata gac gaa aaa gaa gta tct cta ccc atc aag agc cac        336
Ser Ser Glu Ile Asp Glu Lys Glu Val Ser Leu Pro Ile Lys Ser His
            100                 105                 110 aac gat gcg ttc atg ttc gtt tgt tct tca aat gat gga tcc gca ctc        384
Asn Asp Ala Phe Met Phe Val Cys Ser Ser Asn Asp Gly Ser Ala Leu
        115                 120                 125 cag tgt gat gtt ttc gcc ctt gat aac acc aac tct agc gac ggg tgg        432
Gln Cys Asp Val Phe Ala Leu Asp Asn Thr Asn Ser Ser Asp Gly Trp
    130                 135                 140 aaa gtg aat acc gtg gat ctt ggc gtc agc gtt agt ccg gat ttg gca        480
Lys Val Asn Thr Val Asp Leu Gly Val Ser Val Ser Pro Asp Leu Ala
145                 150                 155                 160 ttc gga ctc act gca gat ggg gtc aag gtg aag aag ttg tac gca agc        528
Phe Gly Leu Thr Ala Asp Gly Val Lys Val Lys Lys Leu Tyr Ala Ser
                165                 170                 175 agc ggc ctg aca gcg atc aac gac gac cct tcc ttg ggg tgc aag gct        576
Ser Gly Leu Thr Ala Ile Asn Asp Asp Pro Ser Leu Gly Cys Lys Ala
            180                 185                 190 cct ccc cat tct ccg ccg gcc gga gag gaa ccg agt ttg ccg tcg cct        624
Pro Pro His Ser Pro Pro Ala Gly Glu Glu Pro Ser Leu Pro Ser Pro
        195                 200                 205 gaa aac agc ggg tct gca aca cca gcg gaa gaa agt ccg tct gag tct        672
Glu Asn Ser Gly Ser Ala Thr Pro Ala Glu Glu Ser Pro Ser Glu Ser
    210                 215                 220 gaa tct                                                                678
Glu Ser
225

<210> SEQ ID NO 12
<211> LENGTH: 226
<212> TYPE: PRT
<213> ORGANISM: Toxoplasma gondii

<400> SEQUENCE: 12

Asn Glu Pro Val Ala Leu Ala Gln Leu Ser Thr Phe Leu Glu Leu Val
1               5                   10                  15

Glu Val Pro Cys Asn Ser Val His Val Gln Gly Val Met Thr Pro Asn
            20                  25                  30

Gln Met Val Lys Val Thr Gly Ala Gly Trp Asp Asn Gly Val Leu Glu
        35                  40                  45

Phe Tyr Val Thr Arg Pro Thr Lys Thr Gly Gly Asp Thr Ser Arg Ser
    50                  55                  60
```

```
His Leu Ala Ser Ile Met Cys Tyr Ser Lys Asp Ile Asp Gly Val Pro
 65                  70                  75                  80

Ser Asp Lys Ala Gly Lys Cys Phe Leu Lys Asn Phe Ser Gly Glu Asp
                 85                  90                  95

Ser Ser Glu Ile Asp Glu Lys Glu Val Ser Leu Pro Ile Lys Ser His
            100                 105                 110

Asn Asp Ala Phe Met Phe Val Cys Ser Ser Asn Asp Gly Ser Ala Leu
        115                 120                 125

Gln Cys Asp Val Phe Ala Leu Asp Asn Thr Asn Ser Ser Asp Gly Trp
    130                 135                 140

Lys Val Asn Thr Val Asp Leu Gly Val Ser Val Ser Pro Asp Leu Ala
145                 150                 155                 160

Phe Gly Leu Thr Ala Asp Gly Val Lys Val Lys Leu Tyr Ala Ser
                165                 170                 175

Ser Gly Leu Thr Ala Ile Asn Asp Asp Pro Ser Leu Gly Cys Lys Ala
            180                 185                 190

Pro Pro His Ser Pro Pro Ala Gly Glu Glu Pro Ser Leu Pro Ser Pro
        195                 200                 205

Glu Asn Ser Gly Ser Ala Thr Pro Ala Glu Glu Ser Pro Ser Glu Ser
    210                 215                 220

Glu Ser
225
```

<210> SEQ ID NO 13
<211> LENGTH: 26
<212> TYPE: DNA
<213> ORGANISM: Artificial Sequence
<220> FEATURE:
<223> OTHER INFORMATION: Primer K551

<400> SEQUENCE: 13
ggactagtcg gctcccccag gatgcc        26

<210> SEQ ID NO 14
<211> LENGTH: 44
<212> TYPE: DNA
<213> ORGANISM: Artificial Sequence
<220> FEATURE:
<223> OTHER INFORMATION: Primer K553

<400> SEQUENCE: 14
catccagtcc tgctaccgcc accagaccag acgccacatc cagc        44

<210> SEQ ID NO 15
<211> LENGTH: 44
<212> TYPE: DNA
<213> ORGANISM: Artificial Sequence
<220> FEATURE:
<223> OTHER INFORMATION: Primer K552

<400> SEQUENCE: 15
gtggcgtctg gtctggtggc ggtagcagga ctggatgtca tgcc        44

<210> SEQ ID NO 16
<211> LENGTH: 45
<212> TYPE: DNA
<213> ORGANISM: Artificial Sequence
<220> FEATURE:
<223> OTHER INFORMATION: Primer K555

<400> SEQUENCE: 16
tgacgaccga gctaccgcca ccagagttat cgcatttgca ggatg    45

<210> SEQ ID NO 17
<211> LENGTH: 45
<212> TYPE: DNA
<213> ORGANISM: Artificial Sequence
<220> FEATURE:
<223> OTHER INFORMATION: Primer K554

<400> SEQUENCE: 17
atgcgataac tctggtggcg gtagctcggt cgtcaataat gtcgc    45

<210> SEQ ID NO 18
<211> LENGTH: 31
<212> TYPE: DNA
<213> ORGANISM: Artificial Sequence
<220> FEATURE:
<223> OTHER INFORMATION: Primer 556

<400> SEQUENCE: 18
ccgcggccgc tagccgattt tgctgaccct g    31

<210> SEQ ID NO 19
<211> LENGTH: 33
<212> TYPE: DNA
<213> ORGANISM: Artificial Sequence
<220> FEATURE:
<223> OTHER INFORMATION: Primer K563

<400> SEQUENCE: 19
ggactagtcg gctggctgcc ttgggaggcc ttg    33

<210> SEQ ID NO 20
<211> LENGTH: 45
<212> TYPE: DNA
<213> ORGANISM: Artificial Sequence
<220> FEATURE:
<223> OTHER INFORMATION: Primer K565

<400> SEQUENCE: 20
gccgcggtag cactaccgcc accagacaaa ccagggcgat ctgtg    45

<210> SEQ ID NO 21
<211> LENGTH: 44
<212> TYPE: DNA
<213> ORGANISM: Artificial Sequence
<220> FEATURE:
<223> OTHER INFORMATION: Primer K564

<400> SEQUENCE: 21
gccctggttt gtctggtggc ggtagtgcta ccgcggccac cgcg    44

<210> SEQ ID NO 22
<211> LENGTH: 46
<212> TYPE: DNA
<213> ORGANISM: Artificial Sequence
<220> FEATURE:
<223> OTHER INFORMATION: Primer K567

<400> SEQUENCE: 22
ccggttcgtt actaccgcca ccagagaaat gaacttcttc ttgttc    46

<210> SEQ ID NO 23
<211> LENGTH: 46
<212> TYPE: DNA
<213> ORGANISM: Artificial Sequence -continued
<220> FEATURE:
<223> OTHER INFORMATION: Primer K566

<400> SEQUENCE: 23
gaagttcatt tctctggtgg cggtagtaac gaaccggtgg ccctag          46

<210> SEQ ID NO 24
<211> LENGTH: 30
<212> TYPE: DNA
<213> ORGANISM: Artificial Sequence
<220> FEATURE:
<223> OTHER INFORMATION: Primer K568

<400> SEQUENCE: 24
ccgcggccgc agattcagac tcagacggac                            30

<210> SEQ ID NO 25
<211> LENGTH: 40
<212> TYPE: DNA
<213> ORGANISM: Artificial Sequence
<220> FEATURE:
<223> OTHER INFORMATION: Primer K572

<400> SEQUENCE: 25
cgttactacc gccaccagag ttatcgcatt tgcaggatga                 40

<210> SEQ ID NO 26
<211> LENGTH: 39
<212> TYPE: DNA
<213> ORGANISM: Artificial Sequence
<220> FEATURE:
<223> OTHER INFORMATION: Primer K571

<400> SEQUENCE: 26
taactctggt ggcggtagta acgaaccggt ggccctagc                  39

<210> SEQ ID NO 27
<211> LENGTH: 894
<212> TYPE: DNA
<213> ORGANISM: Artificial Sequence
<220> FEATURE:
<223> OTHER INFORMATION: First chimeric antigen
<220> FEATURE:
<221> NAME/KEY: CDS
<222> LOCATION: (1)..(894)

<400> SEQUENCE: 27

```
act agt cgg ctc ccc cag gat gcc att tgc tcg gat tgg tcc gca tgg      48
Thr Ser Arg Leu Pro Gln Asp Ala Ile Cys Ser Asp Trp Ser Ala Trp
1               5                   10                  15 agc ccc tgc agt gta tcc tgc ggt gac gga agc caa atc agg acg cga      96
Ser Pro Cys Ser Val Ser Cys Gly Asp Gly Ser Gln Ile Arg Thr Arg
            20                  25                  30 act gag gtt tct gct ccg caa cct gga aca cca aca tgt ccg gac tgc     144
Thr Glu Val Ser Ala Pro Gln Pro Gly Thr Pro Thr Cys Pro Asp Cys
        35                  40                  45 cct gcg ccc atg gga agg act tgc gtg gaa caa ggc gga ctt gaa gaa     192
Pro Ala Pro Met Gly Arg Thr Cys Val Glu Gln Gly Gly Leu Glu Glu
    50                  55                  60 atc cgt gaa tgc agt gcg ggg gta tgt gct gtt gac gct gga tgt ggc     240
Ile Arg Glu Cys Ser Ala Gly Val Cys Ala Val Asp Ala Gly Cys Gly
65                  70                  75                  80 gtc tgg tct ggt ggc ggt agc agg act gga tgt cat gcc ttc agg gag     288
Val Trp Ser Gly Gly Gly Ser Arg Thr Gly Cys His Ala Phe Arg Glu
                85                  90                  95
```

-continued

```
aac tgc agc cct ggt aga tgt att gat gac gcc tcg cat gag aat ggc    336
Asn Cys Ser Pro Gly Arg Cys Ile Asp Asp Ala Ser His Glu Asn Gly
            100                 105                 110 tac acc tgc gag tgc ccc aca ggg tac tca cgt gag gtg act tcc aag    384
Tyr Thr Cys Glu Cys Pro Thr Gly Tyr Ser Arg Glu Val Thr Ser Lys
        115                 120                 125 gcg gag gag tcg tgt gtg gaa gga gtc gaa gtc acg ctg gct gag aaa    432
Ala Glu Glu Ser Cys Val Glu Gly Val Glu Val Thr Leu Ala Glu Lys
    130                 135                 140 tgc gag aag gaa ttc ggc atc agc gcg tca tcc tgc aaa tgc gat aac    480
Cys Glu Lys Glu Phe Gly Ile Ser Ala Ser Ser Cys Lys Cys Asp Asn
145                 150                 155                 160 tct ggt ggc ggt agc tcg gtc gtc aat aat gtc gca agg tgc tcc tac    528
Ser Gly Gly Gly Ser Ser Val Val Asn Asn Val Ala Arg Cys Ser Tyr
                165                 170                 175 ggt gca gac agc act ctt ggt cct gtc aag ttg tct gcg gaa gga ccc    576
Gly Ala Asp Ser Thr Leu Gly Pro Val Lys Leu Ser Ala Glu Gly Pro
            180                 185                 190 act aca atg acc ctc gtg tgc ggg aaa gat gga gtc aaa gtt cct caa    624
Thr Thr Met Thr Leu Val Cys Gly Lys Asp Gly Val Lys Val Pro Gln
        195                 200                 205 gac aac aat cag tac tgt tcc ggg acg acg ctg act ggt tgc aac gag    672
Asp Asn Asn Gln Tyr Cys Ser Gly Thr Thr Leu Thr Gly Cys Asn Glu
    210                 215                 220 aaa tcg ttc aaa gat att ttg cca aaa tta act gag aac ccg tgg cag    720
Lys Ser Phe Lys Asp Ile Leu Pro Lys Leu Thr Glu Asn Pro Trp Gln
225                 230                 235                 240 ggt aac gct tcg agt gat aag ggt gcc acg cta acg atc aag aag gaa    768
Gly Asn Ala Ser Ser Asp Lys Gly Ala Thr Leu Thr Ile Lys Lys Glu
                245                 250                 255 gca ttt cca gcc gag tca aaa agc gtc att att gga tgc aca ggg gga    816
Ala Phe Pro Ala Glu Ser Lys Ser Val Ile Ile Gly Cys Thr Gly Gly
            260                 265                 270 tcg cct gag aag cat cac tgt acc gtg aaa ctg gag ttt gcc ggg gct    864
Ser Pro Glu Lys His His Cys Thr Val Lys Leu Glu Phe Ala Gly Ala
        275                 280                 285 gca ggg tca gca aaa tcg gct agc ggc cgc                            894
Ala Gly Ser Ala Lys Ser Ala Ser Gly Arg
    290                 295
```

<210> SEQ ID NO 28
<211> LENGTH: 298
<212> TYPE: PRT
<213> ORGANISM: Artificial Sequence
<220> FEATURE:
<223> OTHER INFORMATION: Synthetic Construct

<400> SEQUENCE: 28

```
Thr Ser Arg Leu Pro Gln Asp Ala Ile Cys Ser Asp Trp Ser Ala Trp
1               5                   10                  15

Ser Pro Cys Ser Val Ser Cys Gly Asp Gly Ser Gln Ile Arg Thr Arg
                20                  25                  30

Thr Glu Val Ser Ala Pro Gln Pro Gly Thr Pro Thr Cys Pro Asp Cys
            35                  40                  45

Pro Ala Pro Met Gly Arg Thr Cys Val Glu Gln Gly Gly Leu Glu Glu
        50                  55                  60

Ile Arg Glu Cys Ser Ala Gly Val Cys Ala Val Asp Ala Gly Cys Gly
65                  70                  75                  80

Val Trp Ser Gly Gly Gly Ser Arg Thr Gly Cys His Ala Phe Arg Glu
```

-continued

```
                    85                  90                  95
Asn Cys Ser Pro Gly Arg Cys Ile Asp Asp Ala Ser His Glu Asn Gly
                100                 105                 110

Tyr Thr Cys Glu Cys Pro Thr Gly Tyr Ser Arg Glu Val Thr Ser Lys
            115                 120                 125

Ala Glu Glu Ser Cys Val Glu Gly Val Glu Val Thr Leu Ala Glu Lys
        130                 135                 140

Cys Glu Lys Glu Phe Gly Ile Ser Ala Ser Ser Cys Lys Cys Asp Asn
145                 150                 155                 160

Ser Gly Gly Gly Ser Ser Val Val Asn Asn Val Ala Arg Cys Ser Tyr
                165                 170                 175

Gly Ala Asp Ser Thr Leu Gly Pro Val Lys Leu Ser Ala Glu Gly Pro
            180                 185                 190

Thr Thr Met Thr Leu Val Cys Gly Lys Asp Gly Val Lys Val Pro Gln
        195                 200                 205

Asp Asn Asn Gln Tyr Cys Ser Gly Thr Thr Leu Thr Gly Cys Asn Glu
    210                 215                 220

Lys Ser Phe Lys Asp Ile Leu Pro Lys Leu Thr Glu Asn Pro Trp Gln
225                 230                 235                 240

Gly Asn Ala Ser Ser Asp Lys Gly Ala Thr Leu Thr Ile Lys Lys Glu
                245                 250                 255

Ala Phe Pro Ala Glu Ser Lys Ser Val Ile Ile Gly Cys Thr Gly Gly
            260                 265                 270

Ser Pro Glu Lys His His Cys Thr Val Lys Leu Glu Phe Ala Gly Ala
        275                 280                 285

Ala Gly Ser Ala Lys Ser Ala Ser Gly Arg
    290                 295

<210> SEQ ID NO 29
<211> LENGTH: 1258
<212> TYPE: DNA
<213> ORGANISM: Artificial Sequence
<220> FEATURE:
<223> OTHER INFORMATION: Second chimeric antigen
<220> FEATURE:
<221> NAME/KEY: CDS
<222> LOCATION: (1)..(1257)

<400> SEQUENCE: 29 act agt cgg ctg gct gcc ttg gga ggc ctt gcg gat cag cct gaa aat    48
Thr Ser Arg Leu Ala Ala Leu Gly Gly Leu Ala Asp Gln Pro Glu Asn
1               5                   10                  15 cat cag gct ctt gca gaa cca gtt acg ggt gtg ggg gaa gca gga gtg    96
His Gln Ala Leu Ala Glu Pro Val Thr Gly Val Gly Glu Ala Gly Val
                20                  25                  30 tcc ccc gtc aac gaa gct ggt gag tca tac agt tct gca act tcg ggt   144
Ser Pro Val Asn Glu Ala Gly Glu Ser Tyr Ser Ser Ala Thr Ser Gly
            35                  40                  45 gtc caa gaa gct acc gcc cca ggt gca gtg ctc ctg gac gca atc gat   192
Val Gln Glu Ala Thr Ala Pro Gly Ala Val Leu Leu Asp Ala Ile Asp
        50                  55                  60 gcc gag tcg gat aag gtg gac aat cag gcg gag gga ggt gag cgt atg   240
Ala Glu Ser Asp Lys Val Asp Asn Gln Ala Glu Gly Gly Glu Arg Met
65                  70                  75                  80 aag aag gtc gaa gag gag ttg tcg tta ttg agg cgg gaa tta tat gat   288
Lys Lys Val Glu Glu Glu Leu Ser Leu Leu Arg Arg Glu Leu Tyr Asp
                85                  90                  95 cgc aca gat cgc cct ggt ttg tct ggt ggc ggt agt gct acc gcg gcc   336
```

```
                                                          -continued

Arg Thr Asp Arg Pro Gly Leu Ser Gly Gly Ser Ala Thr Ala Ala
            100                 105                 110 acc gcg tca gat gac gaa ctg atg agt cga atc cga aat tct gac ttt       384
Thr Ala Ser Asp Asp Glu Leu Met Ser Arg Ile Arg Asn Ser Asp Phe
        115                 120                 125 ttc gat ggt caa gca ccc gtt gac agt ctc aga ccg acg aac gcc ggt       432
Phe Asp Gly Gln Ala Pro Val Asp Ser Leu Arg Pro Thr Asn Ala Gly
130                 135                 140 gtc gac tcg aaa ggg acc gac gat cac ctc acc acc agc atg gat aag       480
Val Asp Ser Lys Gly Thr Asp Asp His Leu Thr Thr Ser Met Asp Lys
145                 150                 155                 160 gca tct gta gag agt cag ctt ccg aga aga gag cca ttg gag acg gag       528
Ala Ser Val Glu Ser Gln Leu Pro Arg Arg Glu Pro Leu Glu Thr Glu
                165                 170                 175 cca gat gaa caa gaa gaa gtt cat ttc tct ggt ggc ggt agt aac gaa       576
Pro Asp Glu Gln Glu Glu Val His Phe Ser Gly Gly Gly Ser Asn Glu
            180                 185                 190 ccg gtg gcc cta gct cag ctc agc aca ttc ctc gag ctc gtc gag gtg       624
Pro Val Ala Leu Ala Gln Leu Ser Thr Phe Leu Glu Leu Val Glu Val
        195                 200                 205 cca tgt aac tct gtt cat gtt cag ggg gtg atg acc ccg aat caa atg       672
Pro Cys Asn Ser Val His Val Gln Gly Val Met Thr Pro Asn Gln Met
210                 215                 220 gtc aaa gtg act ggt gca gga tgg gat aat ggc gtt ctc gag ttc tat       720
Val Lys Val Thr Gly Ala Gly Trp Asp Asn Gly Val Leu Glu Phe Tyr
225                 230                 235                 240 gtc acg agg cca acg aag aca ggc ggg gac aca agc cga agc cat ctt       768
Val Thr Arg Pro Thr Lys Thr Gly Gly Asp Thr Ser Arg Ser His Leu
                245                 250                 255 gcg tcg atc atg tgt tat tcc aag gac att gac ggc gtg ccg tca gac       816
Ala Ser Ile Met Cys Tyr Ser Lys Asp Ile Asp Gly Val Pro Ser Asp
            260                 265                 270 aaa gcg gga aag tgc ttt ctg aag aac ttt tct ggt gaa gac tcg tcg       864
Lys Ala Gly Lys Cys Phe Leu Lys Asn Phe Ser Gly Glu Asp Ser Ser
        275                 280                 285 gaa ata gac gaa aaa gaa gta tct cta ccc atc aag agc cac aac gat       912
Glu Ile Asp Glu Lys Glu Val Ser Leu Pro Ile Lys Ser His Asn Asp
290                 295                 300 gcg ttc atg ttc gtt tgt tct tca aat gat gga tcc gca ctc cag tgt       960
Ala Phe Met Phe Val Cys Ser Ser Asn Asp Gly Ser Ala Leu Gln Cys
305                 310                 315                 320 gat gtt ttc gcc ctt gat aac acc aac tct agc gac ggg tgg aaa gtg      1008
Asp Val Phe Ala Leu Asp Asn Thr Asn Ser Ser Asp Gly Trp Lys Val
                325                 330                 335 aat acc gtg gat ctt ggc gtc agc gtt agt ccg gat ttg gca ttc gga      1056
Asn Thr Val Asp Leu Gly Val Ser Val Ser Pro Asp Leu Ala Phe Gly
            340                 345                 350 ctc act gca gat ggg gtc aag gtg aag aag ttg tac gca agc agc ggc      1104
Leu Thr Ala Asp Gly Val Lys Val Lys Lys Leu Tyr Ala Ser Ser Gly
        355                 360                 365 ctg aca gcg atc aac gac gac cct tcc ttg ggg tgc aag gct cct ccc      1152
Leu Thr Ala Ile Asn Asp Asp Pro Ser Leu Gly Cys Lys Ala Pro Pro
370                 375                 380 cat tct ccg ccg gcc gga gag gaa ccg agt ttg ccg tcg cct gaa aac      1200
His Ser Pro Pro Ala Gly Glu Glu Pro Ser Leu Pro Ser Pro Glu Asn
385                 390                 395                 400 agc ggg tct gca aca cca gcg gaa gaa agt ccg tct gag tct gaa tct      1248
Ser Gly Ser Ala Thr Pro Ala Glu Glu Ser Pro Ser Glu Ser Glu Ser
                405                 410                 415
```

```
gcg gcc gcg g                                                    1258
Ala Ala Ala <210> SEQ ID NO 30
<211> LENGTH: 419
<212> TYPE: PRT
<213> ORGANISM: Artificial Sequence
<220> FEATURE:
<223> OTHER INFORMATION: Synthetic Construct

<400> SEQUENCE: 30

Thr Ser Arg Leu Ala Ala Leu Gly Gly Leu Ala Asp Gln Pro Glu Asn
1               5                   10                  15

His Gln Ala Leu Ala Glu Pro Val Thr Gly Val Gly Glu Ala Gly Val
            20                  25                  30

Ser Pro Val Asn Glu Ala Gly Glu Ser Tyr Ser Ser Ala Thr Ser Gly
        35                  40                  45

Val Gln Glu Ala Thr Ala Pro Gly Ala Val Leu Leu Asp Ala Ile Asp
    50                  55                  60

Ala Glu Ser Asp Lys Val Asp Asn Gln Ala Glu Gly Gly Glu Arg Met
65                  70                  75                  80

Lys Lys Val Glu Glu Glu Leu Ser Leu Leu Arg Arg Glu Leu Tyr Asp
                85                  90                  95

Arg Thr Asp Arg Pro Gly Leu Ser Gly Gly Ser Ala Thr Ala Ala
            100                 105                 110

Thr Ala Ser Asp Asp Glu Leu Met Ser Arg Ile Arg Asn Ser Asp Phe
        115                 120                 125

Phe Asp Gly Gln Ala Pro Val Asp Ser Leu Arg Pro Thr Asn Ala Gly
    130                 135                 140

Val Asp Ser Lys Gly Thr Asp Asp His Leu Thr Thr Ser Met Asp Lys
145                 150                 155                 160

Ala Ser Val Glu Ser Gln Leu Pro Arg Arg Glu Pro Leu Glu Thr Glu
                165                 170                 175

Pro Asp Glu Gln Glu Glu Val His Phe Ser Gly Gly Gly Ser Asn Glu
            180                 185                 190

Pro Val Ala Leu Ala Gln Leu Ser Thr Phe Leu Glu Leu Val Glu Val
        195                 200                 205

Pro Cys Asn Ser Val His Val Gln Gly Val Met Thr Pro Asn Gln Met
    210                 215                 220

Val Lys Val Thr Gly Ala Gly Trp Asp Asn Gly Val Leu Glu Phe Tyr
225                 230                 235                 240

Val Thr Arg Pro Thr Lys Thr Gly Gly Asp Thr Ser Arg Ser His Leu
                245                 250                 255

Ala Ser Ile Met Cys Tyr Ser Lys Ile Asp Gly Val Pro Ser Asp
            260                 265                 270

Lys Ala Gly Lys Cys Phe Leu Lys Asn Phe Ser Gly Glu Asp Ser Ser
        275                 280                 285

Glu Ile Asp Glu Lys Glu Val Ser Leu Pro Ile Lys Ser His Asn Asp
    290                 295                 300

Ala Phe Met Phe Val Cys Ser Ser Asn Asp Gly Ser Ala Leu Gln Cys
305                 310                 315                 320

Asp Val Phe Ala Leu Asp Asn Thr Asn Ser Ser Asp Gly Trp Lys Val
                325                 330                 335

Asn Thr Val Asp Leu Gly Val Ser Val Ser Pro Asp Leu Ala Phe Gly
            340                 345                 350
```

```
Leu Thr Ala Asp Gly Val Lys Val Lys Lys Leu Tyr Ala Ser Ser Gly
        355                 360                 365

Leu Thr Ala Ile Asn Asp Asp Pro Ser Leu Gly Cys Lys Ala Pro Pro
    370                 375                 380

His Ser Pro Pro Ala Gly Glu Glu Pro Ser Leu Pro Ser Pro Glu Asn
385                 390                 395                 400

Ser Gly Ser Ala Thr Pro Ala Glu Glu Ser Pro Ser Glu Ser Glu Ser
                405                 410                 415

Ala Ala Ala

<210> SEQ ID NO 31
<211> LENGTH: 1183
<212> TYPE: DNA
<213> ORGANISM: Artificial Sequence
<220> FEATURE:
<223> OTHER INFORMATION: Third chimeric antigen
<220> FEATURE:
<221> NAME/KEY: CDS
<222> LOCATION: (1)..(1182)

<400> SEQUENCE: 31 act agt cgg ctc ccc cag gat gcc att tgc tcg gat tgg tcc gca tgg      48
Thr Ser Arg Leu Pro Gln Asp Ala Ile Cys Ser Asp Trp Ser Ala Trp
1               5                   10                  15 agc ccc tgc agt gta tcc tgc ggt gac gga agc caa atc agg acg cga      96
Ser Pro Cys Ser Val Ser Cys Gly Asp Gly Ser Gln Ile Arg Thr Arg
            20                  25                  30 act gag gtt tct gct ccg caa cct gga aca cca aca tgt ccg gac tgc     144
Thr Glu Val Ser Ala Pro Gln Pro Gly Thr Pro Thr Cys Pro Asp Cys
        35                  40                  45 ccc gcg ccc atg gga agg act tgc gtg gaa caa ggc gga ctt gaa gaa     192
Pro Ala Pro Met Gly Arg Thr Cys Val Glu Gln Gly Gly Leu Glu Glu
    50                  55                  60 atc cgt gaa tgc agt gcg ggg gta tgt gct gtt gac gct gga tgt ggc     240
Ile Arg Glu Cys Ser Ala Gly Val Cys Ala Val Asp Ala Gly Cys Gly
65                  70                  75                  80 gtc tgg tct ggt ggc ggt agc agg act gga tgt cat gcc ttc agg gag     288
Val Trp Ser Gly Gly Gly Ser Arg Thr Gly Cys His Ala Phe Arg Glu
                85                  90                  95 aac tgc cgc cct ggt aga tgt att gat gac gcc tcg cat gag aat ggc     336
Asn Cys Arg Pro Gly Arg Cys Ile Asp Asp Ala Ser His Glu Asn Gly
            100                 105                 110 tac acc tgc gag tgc ccc aca tgg tac tca cgt gag gtg act tcc aag     384
Tyr Thr Cys Glu Cys Pro Thr Trp Tyr Ser Arg Glu Val Thr Ser Lys
        115                 120                 125 gcg gag gag tcg tgt gtg gaa gga gtc gaa gtc acg ctg gct gag aaa     432
Ala Glu Glu Ser Cys Val Glu Gly Val Glu Val Thr Leu Ala Glu Lys
    130                 135                 140 tgc gag aag gaa ttc ggc atc agc gcg tcc tcc tgc aaa tgc gat aac     480
Cys Glu Lys Glu Phe Gly Ile Ser Ala Ser Ser Cys Lys Cys Asp Asn
145                 150                 155                 160 tct ggt ggc ggt agt aac gaa ccg gtg gcc cta gct cag ctc agc aca     528
Ser Gly Gly Gly Ser Asn Glu Pro Val Ala Leu Ala Gln Leu Ser Thr
                165                 170                 175 ttc ctc gag ctc gtc gag gtg cca tgt aac tct gtt cat gtt cag ggg     576
Phe Leu Glu Leu Val Glu Val Pro Cys Asn Ser Val His Val Gln Gly
            180                 185                 190 gtg atg acc ccg aat caa atg gtc aaa gtg act ggt gca gga tgg gat     624
Val Met Thr Pro Asn Gln Met Val Lys Val Thr Gly Ala Gly Trp Asp
        195                 200                 205
```

```
aat ggc gtt ctc gag ttc tat gtc acg agg cca acg aag aca ggc ggg     672
Asn Gly Val Leu Glu Phe Tyr Val Thr Arg Pro Thr Lys Thr Gly Gly
    210                 215                 220 gac aca agc cga agc cac ctt gcg tcg atc atg tgt tat tcc aag gac     720
Asp Thr Ser Arg Ser His Leu Ala Ser Ile Met Cys Tyr Ser Lys Asp
225                 230                 235                 240 att gac ggc gtg ccg tca gac aaa gcg gga aag tgc ttt ttg aag aac     768
Ile Asp Gly Val Pro Ser Asp Lys Ala Gly Lys Cys Phe Leu Lys Asn
                245                 250                 255 ttt tct ggt gaa gac tcg tcg gaa ata gac gaa aaa gaa gta tct cta     816
Phe Ser Gly Glu Asp Ser Ser Glu Ile Asp Glu Lys Glu Val Ser Leu
            260                 265                 270 ccc atc aag agc cac aac gat gcg ttc atg ttc gtt tgt tct tca aat     864
Pro Ile Lys Ser His Asn Asp Ala Phe Met Phe Val Cys Ser Ser Asn
        275                 280                 285 gat gga tcc gca ctc cag tgt gat gtt ttc gcc ctt gat aac acc aac     912
Asp Gly Ser Ala Leu Gln Cys Asp Val Phe Ala Leu Asp Asn Thr Asn
    290                 295                 300 tct agc gac ggg tgg aaa gtg aat acc gtg gat ctt gac gtc agc gtt     960
Ser Ser Asp Gly Trp Lys Val Asn Thr Val Asp Leu Asp Val Ser Val
305                 310                 315                 320 agt ccg gat ttg gca ttc gga ctc act gca gat ggg gtc aag gtg aag    1008
Ser Pro Asp Leu Ala Phe Gly Leu Thr Ala Asp Gly Val Lys Val Lys
                325                 330                 335 aag ttg tac gca agc agc ggc ctg aca gcg atc aac gac gac cct tcc    1056
Lys Leu Tyr Ala Ser Ser Gly Leu Thr Ala Ile Asn Asp Asp Pro Ser
            340                 345                 350 ttg ggg tgc aag gct cct ccc cat tct ccg ccg gcc gga gag gaa ccg    1104
Leu Gly Cys Lys Ala Pro Pro His Ser Pro Pro Ala Gly Glu Glu Pro
        355                 360                 365 agt ttg ccg tcg cct gaa aac agc ggg tct gca aca cca gcg gaa gaa    1152
Ser Leu Pro Ser Pro Glu Asn Ser Gly Ser Ala Thr Pro Ala Glu Glu
    370                 375                 380 agt ccg tct gag tct gaa tct gcg gcc gcg g                          1183
Ser Pro Ser Glu Ser Glu Ser Ala Ala Ala
385                 390

<210> SEQ ID NO 32
<211> LENGTH: 394
<212> TYPE: PRT
<213> ORGANISM: Artificial Sequence
<220> FEATURE:
<223> OTHER INFORMATION: Synthetic Construct

<400> SEQUENCE: 32

Thr Ser Arg Leu Pro Gln Asp Ala Ile Cys Ser Asp Trp Ser Ala Trp
1               5                   10                  15

Ser Pro Cys Ser Val Ser Cys Gly Asp Gly Ser Gln Ile Arg Thr Arg
            20                  25                  30

Thr Glu Val Ser Ala Pro Gln Pro Gly Thr Pro Thr Cys Pro Asp Cys
        35                  40                  45

Pro Ala Pro Met Gly Arg Thr Cys Val Glu Gln Gly Gly Leu Glu Glu
    50                  55                  60

Ile Arg Glu Cys Ser Ala Gly Val Cys Ala Val Asp Ala Gly Cys Gly
65                  70                  75                  80

Val Trp Ser Gly Gly Gly Ser Arg Thr Gly Cys His Ala Phe Arg Glu
                85                  90                  95

Asn Cys Arg Pro Gly Arg Cys Ile Asp Asp Ala Ser His Glu Asn Gly
            100                 105                 110
```

```
Tyr Thr Cys Glu Cys Pro Thr Trp Tyr Ser Arg Glu Val Thr Ser Lys
            115                 120                 125

Ala Glu Glu Ser Cys Val Gly Val Glu Val Thr Leu Ala Glu Lys
        130                 135                 140

Cys Glu Lys Glu Phe Gly Ile Ser Ala Ser Cys Lys Cys Asp Asn
145                 150                 155                 160

Ser Gly Gly Gly Ser Asn Glu Pro Val Ala Leu Ala Gln Leu Ser Thr
                165                 170                 175

Phe Leu Glu Leu Val Glu Val Pro Cys Asn Ser Val His Val Gln Gly
            180                 185                 190

Val Met Thr Pro Asn Gln Met Val Lys Val Thr Gly Ala Gly Trp Asp
        195                 200                 205

Asn Gly Val Leu Glu Phe Tyr Val Thr Arg Pro Thr Lys Thr Gly Gly
    210                 215                 220

Asp Thr Ser Arg Ser His Leu Ala Ser Ile Met Cys Tyr Ser Lys Asp
225                 230                 235                 240

Ile Asp Gly Val Pro Ser Asp Lys Ala Gly Lys Cys Phe Leu Lys Asn
                245                 250                 255

Phe Ser Gly Glu Asp Ser Ser Glu Ile Asp Glu Lys Glu Val Ser Leu
            260                 265                 270

Pro Ile Lys Ser His Asn Asp Ala Phe Met Phe Val Cys Ser Ser Asn
        275                 280                 285

Asp Gly Ser Ala Leu Gln Cys Asp Val Phe Ala Leu Asp Asn Thr Asn
    290                 295                 300

Ser Ser Asp Gly Trp Lys Val Asn Thr Val Asp Leu Asp Val Ser Val
305                 310                 315                 320

Ser Pro Asp Leu Ala Phe Gly Leu Thr Ala Asp Gly Val Lys Val Lys
                325                 330                 335

Lys Leu Tyr Ala Ser Ser Gly Leu Thr Ala Ile Asn Asp Asp Pro Ser
            340                 345                 350

Leu Gly Cys Lys Ala Pro Pro His Ser Pro Ala Gly Glu Glu Pro
        355                 360                 365

Ser Leu Pro Ser Pro Glu Asn Ser Gly Ser Ala Thr Pro Ala Glu Glu
    370                 375                 380

Ser Pro Ser Glu Ser Glu Ser Ala Ala Ala
385                 390

<210> SEQ ID NO 33
<211> LENGTH: 115
<212> TYPE: PRT
<213> ORGANISM: Toxoplasma gondii

<400> SEQUENCE: 33

Ser Gly Gly Thr Gly Gln Gly Leu Gly Ile Gly Glu Ser Val Asp Leu
1               5                   10                  15

Glu Met Met Gly Asn Thr Tyr Arg Val Glu Arg Pro Thr Gly Asn Pro
            20                  25                  30

Asp Leu Leu Lys Ile Ala Ile Lys Ala Ser Asp Gly Ser Tyr Ser Glu
        35                  40                  45

Val Gly Asn Val Asn Val Glu Glu Val Ile Asp Thr Met Lys Ser Met
    50                  55                  60

Gln Arg Asp Glu Asp Ile Phe Leu Arg Ala Leu Asn Lys Gly Glu Thr
65                  70                  75                  80

Val Glu Glu Ala Ile Glu Asp Val Ala Gln Ala Glu Gly Leu Asn Ser
                85                  90                  95
```

```
Glu Gln Thr Leu Gln Leu Glu Asp Ala Val Ser Ala Val Ala Ser Trp
                100                 105                 110

Gln Asp Glu
        115

<210> SEQ ID NO 34
<211> LENGTH: 53
<212> TYPE: PRT
<213> ORGANISM: Toxoplasma gondii

<400> SEQUENCE: 34

Tyr Ser Ser Pro Arg Ile Val Val Leu Ile Arg Tyr Cys Phe Phe Ser
1               5                   10                  15

Thr Tyr Arg Leu Thr Met Phe Ala Val Lys His Cys Leu Leu Trp Ala
            20                  25                  30

Val Gly Ala Leu Val Asn Val Ser Val Arg Ala Ala Glu Phe Ser Gly
        35                  40                  45

Trp Asn Gln Gly Pro
    50

<210> SEQ ID NO 35
<211> LENGTH: 35
<212> TYPE: PRT
<213> ORGANISM: Toxoplasma gondii

<400> SEQUENCE: 35

Glu Asn Pro Val Arg Pro Pro Pro Gly Phe His Pro Ser Val Ile
1               5                   10                  15

Pro Asn Pro Pro Tyr Pro Leu Gly Thr Pro Ala Gly Met Pro Gln Pro
            20                  25                  30

Glu Val Pro
        35

<210> SEQ ID NO 36
<211> LENGTH: 90
<212> TYPE: PRT
<213> ORGANISM: Toxoplasma gondii

<400> SEQUENCE: 36

Ala Pro Thr Gln Ser Glu Met Lys Glu Phe Gln Glu Glu Ile Lys Glu
1               5                   10                  15

Gly Val Glu Glu Thr Lys His Glu Asp Asp Pro Glu Met Thr Arg Leu
            20                  25                  30

Met Val Thr Glu Lys Gln Glu Ser Lys Asn Phe Ser Lys Met Ala Lys
        35                  40                  45

Ser Gln Ser Phe Ser Thr Arg Ile Glu Glu Leu Gly Gly Ser Ile Ser
    50                  55                  60

Phe Leu Thr Glu Thr Gly Val Thr Met Ile Glu Leu Pro Lys Thr Val
65                  70                  75                  80

Ser Glu His Asp Met Asp Gln Leu Leu His
            85                  90

<210> SEQ ID NO 37
<211> LENGTH: 149
<212> TYPE: PRT
<213> ORGANISM: Toxoplasma gondii

<400> SEQUENCE: 37

Val Met Ala Ser Asp Pro Pro Leu Val Ala Asn Gln Trp Thr Cys Pro
```

```
1               5                  10                 15

Asp Lys Lys Ser Thr Ala Ala Val Ile Leu Thr Pro Thr Glu Asn His
                20                 25                 30

Phe Thr Leu Lys Cys Pro Lys Thr Ala Leu Thr Glu Pro Pro Thr Leu
                35                 40                 45

Ala Tyr Ser Pro Asn Arg Gln Ile Cys Pro Ala Gly Thr Thr Ser Ser
                50                 55                 60

Cys Thr Ser Lys Ala Val Thr Leu Ser Ser Leu Ile Pro Glu Ala Glu
 65                 70                 75                 80

Asp Ser Trp Trp Thr Gly Asp Ser Ala Ser Leu Asp Thr Ala Gly Ile
                85                 90                 95

Lys Leu Thr Val Pro Ile Glu Lys Phe Pro Val Thr Thr Gln Thr Phe
                100                105                110

Trp Gly Cys Ile Lys Gly Asp Ala Gln Ser Cys Met Val Thr Val
                115                120                125

Thr Val Gln Ala Arg Ala Ser Ser Trp Asn Asn Val Ala Arg Cys Ser
                130                135                140

Tyr Gly Ala Asp Ser
145

<210> SEQ ID NO 38
<211> LENGTH: 98
<212> TYPE: PRT
<213> ORGANISM: Toxoplasma gondii

<400> SEQUENCE: 38

Gly Leu Ser Gln Arg Val Pro Glu Leu Pro Glu Val Glu Pro Phe Asp
 1               5                  10                 15

Glu Val Gly Thr Gly Ala Arg Arg Ser Gly Ser Ile Ala Thr Leu Leu
                20                 25                 30

Pro Gln Asp Ala Val Leu Tyr Glu Asn Ser Glu Asp Val Ala Val Pro
                35                 40                 45

Ser Asp Ser Ala Ser Thr Pro Ser Tyr Phe His Val Glu Ser Pro Ser
                50                 55                 60

Ala Ser Val Glu Ala Ala Thr Gly Ala Val Gly Glu Val Val Pro Asp
 65                 70                 75                 80

Cys Glu Glu Gln Gln Glu Gln Gly Asp Thr Thr Leu Ser Asp His Asp
                85                 90                 95

Phe His

<210> SEQ ID NO 39
<211> LENGTH: 135
<212> TYPE: PRT
<213> ORGANISM: Toxoplasma gondii

<400> SEQUENCE: 39

Leu Asn Pro Ile Asp Asp Met Leu Phe Glu Thr Ala Leu Thr Ala Asn
 1               5                  10                 15

Glu Met Met Glu Asp Ile Thr Trp Arg Pro Arg Val Asp Val Glu Phe
                20                 25                 30

Asp Ser Lys Lys Lys Glu Met Ile Ile Leu Ala Asp Leu Pro Gly Leu
                35                 40                 45

Gln Lys Asp Asp Val Thr Ile Glu Val Asp Asn Gly Ala Ile Val Ile
                50                 55                 60

Lys Gly Glu Lys Thr Ser Lys Glu Ala Glu Lys Val Asp Asp Gly Lys
 65                 70                 75                 80
```

-continued

```
Thr Lys Asn Ile Leu Thr Glu Arg Val Ser Gly Tyr Phe Ala Arg Arg
                85                  90                  95

Phe Gln Leu Pro Ser Asn Tyr Lys Pro Asp Gly Ile Ser Ala Ala Met
            100                 105                 110

Asp Asn Gly Val Leu Arg Val Thr Ile Lys Val Glu Asp Ser Gly Gly
        115                 120                 125

Ala Lys Gln Gln Ile Ser Val
    130                 135

<210> SEQ ID NO 40
<211> LENGTH: 144
<212> TYPE: PRT
<213> ORGANISM: Toxoplasma gondii

<400> SEQUENCE: 40

Pro Cys Pro Ile Asn Ala Thr Cys Gly Gln Phe Glu Glu Trp Ser Thr
1               5                   10                  15

Cys Ser Val Ser Cys Gly Gly Gly Leu Lys Thr Arg Ser Arg Asn Pro
            20                  25                  30

Trp Asn Glu Asp Gln Gln His Gly Gly Leu Ser Cys Glu Gln Gln His
        35                  40                  45

Pro Gly Gly Arg Thr Glu Thr Val Thr Cys Asn Pro Gln Ala Cys Pro
    50                  55                  60

Val Asp Glu Arg Pro Gly Glu Trp Ala Glu Trp Gly Glu Cys Ser Val
65                  70                  75                  80

Thr Cys Gly Asp Gly Val Arg Glu Arg Arg Arg Gly Lys Ser Leu Val
                85                  90                  95

Glu Ala Lys Phe Gly Gly Arg Thr Ile Asp Gln Gln Asn Glu Ala Leu
            100                 105                 110

Pro Glu Asp Leu Lys Ile Lys Asn Val Glu Tyr Glu Pro Cys Ser Tyr
        115                 120                 125

Pro Ala Cys Gly Ala Ser Cys Thr Tyr Val Trp Ser Asp Trp Asn Lys
    130                 135                 140

<210> SEQ ID NO 41
<211> LENGTH: 194
<212> TYPE: PRT
<213> ORGANISM: Toxoplasma gondii

<400> SEQUENCE: 41

Leu Arg Gly Tyr Arg Phe Gly Val Trp Lys Lys Gly Arg Cys Leu Asp
1               5                   10                  15

Tyr Thr Glu Leu Thr Asp Thr Val Ile Glu Arg Val Glu Ser Lys Ala
            20                  25                  30

Gln Cys Trp Val Lys Thr Phe Glu Asn Asp Gly Val Ala Ser Asp Gln
        35                  40                  45

Pro His Thr Tyr Pro Leu Thr Ser Gln Ala Ser Trp Asn Asp Trp Trp
    50                  55                  60

Pro Leu His Gln Ser Asp Gln Pro His Ser Gly Gly Val Gly Arg Asn
65                  70                  75                  80

Tyr Gly Phe Tyr Tyr Val Asp Thr Thr Gly Glu Gly Lys Cys Ala Leu
                85                  90                  95

Ser Asp Gln Val Pro Asp Cys Leu Val Ser Asp Ser Ala Ala Val Ser
            100                 105                 110

Tyr Thr Ala Ala Gly Ser Leu Ser Glu Glu Thr Pro Asn Phe Ile Ile
        115                 120                 125
```

```
Pro Ser Asn Pro Ser Val Thr Pro Pro Thr Pro Glu Thr Ala Leu Gln
        130                 135                 140

Cys Thr Ala Asp Lys Phe Pro Asp Ser Phe Gly Ala Cys Asp Val Gln
145                 150                 155                 160

Ala Cys Lys Arg Gln Lys Thr Ser Cys Val Gly Gly Gln Ile Gln Ser
                165                 170                 175

Thr Ser Val Asp Cys Thr Ala Asp Glu Gln Asn Glu Cys Gly Ser Asn
            180                 185                 190

Thr Ala

<210> SEQ ID NO 42
<211> LENGTH: 169
<212> TYPE: PRT
<213> ORGANISM: Toxoplasma gondii

<400> SEQUENCE: 42

Ser Ala Asn Val Thr Ser Ser Glu Pro Ala Lys Leu Asp Leu Ser Cys
1               5                   10                  15

Ala His Ser Asp Asn Lys Gly Ser Arg Ala Pro Thr Ile Gly Glu Pro
            20                  25                  30

Val Pro Asp Val Ser Leu Glu Gln Cys Ala Ala Gln Cys Lys Ala Val
        35                  40                  45

Asp Gly Cys Thr His Phe Thr Tyr Asn Asp Asp Ser Lys Met Cys His
    50                  55                  60

Val Lys Glu Gly Lys Pro Asp Leu Tyr Asp Leu Thr Gly Gly Lys Thr
65                  70                  75                  80

Ala Pro Arg Ser Cys Asp Arg Ser Cys Phe Glu Gln His Val Ser Tyr
                85                  90                  95

Glu Gly Ala Pro Asp Val Met Thr Ala Met Val Thr Ser Gln Ser Ala
            100                 105                 110

Asp Cys Gln Ala Ala Cys Ala Ala Asp Pro Ser Cys Glu Ile Phe Thr
        115                 120                 125

Tyr Asn Glu His Asp Gln Lys Cys Thr Phe Lys Gly Arg Gly Phe Ser
    130                 135                 140

Ala Phe Lys Glu Arg Gly Val Leu Gly Val Thr Ser Gly Pro Lys Gln
145                 150                 155                 160

Phe Cys Asp Glu Gly Gly Lys Leu Thr
                165

<210> SEQ ID NO 43
<211> LENGTH: 33
<212> TYPE: DNA
<213> ORGANISM: Artificial sequence
<220> FEATURE:
<223> OTHER INFORMATION: Synthetic oligonucleotide

<400> SEQUENCE: 43
ggccaagctt gaaatgggta ctagtcggct ccc                               33

<210> SEQ ID NO 44
<211> LENGTH: 32
<212> TYPE: DNA
<213> ORGANISM: Artificial sequence
<220> FEATURE:
<223> OTHER INFORMATION: Synthetic oligonucleotide

<400> SEQUENCE: 44
ccggtctaga gagccgattt tgctgaccct gc                                32
```

```
<210> SEQ ID NO 45
<211> LENGTH: 37
<212> TYPE: DNA
<213> ORGANISM: Artificial sequence
<220> FEATURE:
<223> OTHER INFORMATION: Synthetic oligonucleotide

<400> SEQUENCE: 45
ggccaagctt gaaatggtgg ctgccttggg aggcctt                              37

<210> SEQ ID NO 46
<211> LENGTH: 34
<212> TYPE: DNA
<213> ORGANISM: Artificial sequence
<220> FEATURE:
<223> OTHER INFORMATION: Synthetic oligonucleotide

<400> SEQUENCE: 46
ccggtctaga gctaaccaga agattcagac tcag                                 34

<210> SEQ ID NO 47
<211> LENGTH: 5
<212> TYPE: PRT
<213> ORGANISM: Artificial sequence
<220> FEATURE:
<223> OTHER INFORMATION: Peptide Linker SGGGS

<400> SEQUENCE: 47

Ser Gly Gly Gly Ser
1               5
```